(12) United States Patent
Rajan et al.

(10) Patent No.: US 10,314,308 B2
(45) Date of Patent: Jun. 11, 2019

(54) MICROBIOCIDAL BENZOXABOROLES

(71) Applicant: SYNGENTA PARTICIPATIONS AG, Basel (CH)

(72) Inventors: Ramya Rajan, Corlim Ilhas (IN); Daniel Stierli, Stein (CH); Renaud Beaudegnies, Schaffhauserstrasse (CH); Peter Renold, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/542,695

(22) PCT Filed: Jan. 13, 2016

(86) PCT No.: PCT/EP2016/050562
§ 371 (c)(1),
(2) Date: Jul. 11, 2017

(87) PCT Pub. No.: WO2016/113303
PCT Pub. Date: Jul. 21, 2016

(65) Prior Publication Data
US 2018/0000090 A1 Jan. 4, 2018

(30) Foreign Application Priority Data

Jan. 13, 2015 (IN) .............................. 113/DEL/2015

(51) Int. Cl.
*A01N 55/08* (2006.01)
*C07F 5/02* (2006.01)

(52) U.S. Cl.
CPC .............. *A01N 55/08* (2013.01); *C07F 5/025* (2013.01)

(58) Field of Classification Search
None
See application file for complete search history.

(56) References Cited

U.S. PATENT DOCUMENTS

| | | | |
|---|---|---|---|
| 8,168,614 B2 * | 5/2012 | Baker | A61K 31/69 514/64 |
| 2007/0286822 A1 * | 12/2007 | Sanders | A61K 8/49 424/49 |
| 2011/0207701 A1 * | 8/2011 | Zhou | C07F 5/025 514/64 |

FOREIGN PATENT DOCUMENTS

| | | | |
|---|---|---|---|
| WO | 2011022337 A1 | | 2/2011 |
| WO | WO 2011063293 | * | 5/2011 |
| WO | 2013050591 A2 | | 4/2013 |
| WO | WO 2013050591 | * | 4/2013 |
| WO | 2014173880 A1 | | 10/2014 |
| WO | 2015097276 A1 | | 7/2015 |
| WO | 2015121442 A1 | | 8/2015 |

OTHER PUBLICATIONS

Wu et al.( Synthesis of a novel pyrrolo-benzoxaborolescaffold and its derivatization via Friedel-Crafts reaction catalyzed by anhydrous stannic chloride, Chinese Chemical Letters (2011), 22(12), 1411-1414 CODEN: CCLEE7; ISSN: 1001-8417). (Year: 2011).*
Wu et al. (Novelpyrrolobenzoxaboroles: Design, synthesis, and biological evaluation againstTrypanosoma brucei, European Journal of Medicinal Chemistry (2014), 81,59-75). (Year: 2014).*
International Search Report for Patent Application No. PCT/EP2016/050562 dated Jun. 27, 2016.

* cited by examiner

*Primary Examiner* — Alton N Pryor
(74) *Attorney, Agent, or Firm* — Toni-Junell Herbert; Dinsmore & Shohl LLP

(57) ABSTRACT

Compounds of formula (I) are as defined in the claims, and their use in compositions and methods for the control and/or prevention of microbial infection, particularly fungal infection, in plants and to processes for the preparation of these compounds.

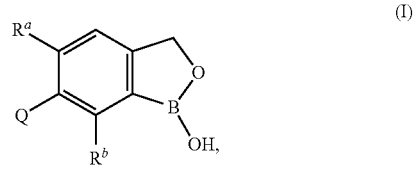

(I)

9 Claims, No Drawings

MICROBIOCIDAL BENZOXABOROLES

CROSS REFERENCE TO RELATED APPLICATIONS

This application is a 371 of International Application No. PCT/EP2016/050562, filed Jan. 13, 2016, which claims priority to IN Application Number 113/DEL/2015, filed Jan. 13, 2015, the contents of which are incorporated herein by reference herein.

The present invention relates to novel microbiocidally active, in particular fungicidally active, oxoborazoles moiety containing compounds their use in compositions and methods for the control and/or prevention of microbial infection, particularly fungal infection, in plants or plant propagation material, harvested food crops by phytopathogenic microorganisms, preferably fungi and to processes for the preparation of these compounds. Preferably these compounds are used in agriculture or horticulture for controlling or preventing infestation of plants by phytopathogenic microorganisms, preferably fungi.

The incidence of serious microbial infections, particularly fungal infections, either systemic or topical, continues to increase for plants.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations continues to be a major problem. Furthermore, fungicide resistance has become a serious problem, rendering these agents ineffective for some agricultural uses. As such, a need exists for the development of new fungicidal compounds with improved antifungal properties. It has been found that novel oxoborazoles with a specific substitution pattern are novel and have improved microbiocidal activity.

The present invention provides a compound of formula (I)

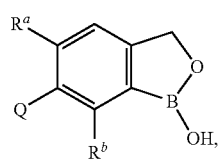

(I)

wherein $R^a$ and $R^b$ is H, fluorine, chlorine, bromine, cyano, nitro, $C_1$-$C_4$alkyl which can be substituted by one to five $R^5$, $C_1$-$C_4$alkoxy which can be substituted by one to five $R^5$, $C_1$-$C_4$haloalkyl which can be substituted by one to five $R^{5a}$;

Q is a five- to ten-membered monocyclic or bicyclic ring system linked via a carbon atom to the rest of the molecule, said ring system is aromatic and can contain 1 to 4 ring members selected from the group consisting of nitrogen, oxygen, —C(O)— and —S(O)$_m$—, it not being possible for each ring system to contain more than 2 oxygen atoms and more than 2 sulfur atoms, said five- to ten-membered ring system which can be can be substituted by one to five $R^5$;

$R^5$ is independently selected from halogen, —OH, —CN, —NO$_2$, —NR$^6$R$^7$, $C_{1-4}$alkyl, $C_{1-4}$haloalkyl, $C_{1-4}$alkoxy, $C_{1-4}$haloalkoxy, $C_{3-6}$cycloalkyl, $C_2$-$C_6$alkenyl, $C_{2-6}$alkynyl, $C_{1-4}$alkylthio, $C_{1-4}$haloalkylthio, —C(O)H, —C(O)(C$_{1-4}$alkoxy), —C(O)(C$_{1-4}$alkyl), —C(O)—NH—(C$_{1-4}$alkyl), —C(O)—N(C$_{1-4}$alkyl)$_2$, $C_1$-$C_4$alkyl, $C_1$-$C_4$haloalkyl, $C_1$-$C_4$alkoxy, $C_1$-$C_4$alkylthio, $C_1$-$C_4$alkoxy-$C_1$-$C_4$alkyl, $C_1$-$C_4$-haloalkoxy, hydroxyimino, $C_1$-$C_4$alkoximino, $C_1$-$C_4$alkoximino $C_1$-$C_4$alkyl and $C_1$-$C_4$alkylendioxy; —C(O)NH(C$_{1-4}$alkyl), —C(O)N(C$_{1-4}$alkyl)(C$_{1-4}$alkyl), —OC(O)NH(C$_{1-4}$alkyl), —OC(O)N(C$_{1-4}$alkyl)(C$_{1-4}$alkyl), —NHC(O)(C$_{1-4}$alkyl), —NHC(O)(C$_{1-4}$alkoxy), —N(C$_{1-4}$alkyl)C(O)(C$_{1-4}$alkyl), —N(C$_{1-4}$alkyl)C(O)(C$_{1-4}$alkoxy), —OC(O)(C$_{1-4}$alkyl), —C(=N—O—(C$_{1-4}$alkyl)—H, —C(=N—O—(C$_{1-4}$alkyl)-$C_1$-$C_4$alkyl;

or $R^5$ is independently selected from a -X-(6 to 10 membered-aryl) group which can be substituted by one to five substituents selected halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;

or $R^5$ is independently selected from a -X-linked-5- or 6-membered heteroaryl group which comprises one or two or three heteroatoms selected from or two N, O and S which can be substituted by one to five substituents selected from halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;

or $R^5$ is independently selected from a -X-linked-5- or 6-membered heterocycloalkyl group which comprises one or two or three heteroatoms selected from or two N, O and S which can be substituted by one to five substituents selected from halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;

$R^{5a}$ is independently selected from $C_1$-$C_4$alkyl, $C_1$-$C_4$haloalkyl, $C_1$-$C_4$alkoxy, $C_1$-$C_4$haloalkoxy, —OH, —CN, —NO$_2$;

$R^6$ and $R^7$ are independently H, —$C_{1-4}$alkyl —$C_{2-4}$alkenyl, —$C_{2-4}$alkynyl or combine with the interjacent nitrogen to form a five- or six-membered heterocyclic ring which may comprise additionally to the interjacent nitrogen atom one or two heteroatoms selected from N, O or S atoms, it not being possible for each ring system to contain more than 2 oxygen atoms and more than 2 sulfur atoms, and this five- or six-membered heterocyclic ring is unsubstituted or this five- or six-membered heterocyclic ring which can be substituted by one to five $R^5$;

X is a direct bond or a bridge selected from —O—, —S(O)$_m$— or —NH—;

m is 0, 1 or 2;

and agronomically acceptable salts and N-oxides of those compounds.

The present invention accordingly further relates to a method for controlling or preventing of infestation of plants or plant propagation material and/or harvested food crops susceptible to microbial attack, preferably susceptible to fungicidal attack, by treating plants or plant propagation material and/or harvested food crops with an effective amount of benzoxaborole derivatives according to formula (I).

The present invention accordingly further relates to the use of benzoxaborole derivatives according to formula (I) for controlling or preventing infestation of plants or plant propagation material and/or harvested food crops susceptible to microbial attack, preferably susceptible to fungicidal attack.

The present invention accordingly further relates to the use of benzoxaborole derivatives according to formula (I) and salts thereof for controlling or preventing infestation of plants or plant propagation material and/or harvested food crops by treating plants or plant propagation material and/or harvested food crops with an effective amount of an benzoxaborole of general formula (I).

Accordingly the present invention also relates to a method of protecting plant propagation material and organs that grow at a later point in time against damage phytopathogenic diseases, which method comprises applying to said propagation material a fungicidally effective amount of a compound of formula I.

In yet a further aspect of the invention, the invention provides plant propagation material treated with a plant propagation material protecting composition comprising a compound of formula (I).

A preferred embodiment of the invention relates to a method of controlling or preventing damage by phytopathogenic diseases in a growing plant or growing plant tissue said method comprising: applying onto the plant propagation material, before planting or sowing thereof a fungicidial effective amount of a compound of formula (I).

A method of controlling or preventing fungal diseases in a growing plant or growing plant tissue said method comprising: applying onto the plant propagation material before planting or sowing thereof a fungicidial effective amount of a compound of formula (I).

In a preferred embodiment the plant propagation material is a seed or a tuber. In a further preferred embodiment the plant propagation material is a seed. In a further preferred embodiment the plant propagation material is a tuber. Preferably the seeds and tubers (stem tubers and root tubers) according to this application are alive. Preferably the seeds and tubers according to this application are able to germinate.

In a further aspect of the invention, the invention provides a method of controlling or preventing damage by phytopathogenic diseases in a growing plant said method comprising applying onto the seed, before planting or sowing thereof a compound of formula (I).

In a further aspect of the invention, the invention provides a method of protecting plant propagation material and organs that grow at a later point in time against damage by phytopathogenic diseases, which method comprises applying to said propagation material a fungicidally effective amount of a compound of formula (I).

In a further aspect of the invention, the invention provides a plant propagation material comprising compound a compound of formula (I). Preferably the plant propargation material comprising a fungicidial effective amount of a compound of formula (I).

In a further aspect of the invention, the invention provides a coated plant propagation material coated with a compound of formula (I).

In a further aspect of the invention, the invention provides a coated plant propagation material coated with coating comprising a compound of formula (I) as defined in claim 1.

In a further aspect of the invention, the invention provides a plant propagation material comprising an outer coating characterized that the outer coating comprises a compound according to formula (I), preferably a seed comprising an outer coating characterized that the outer coating comprises a compound according to formula (I).

In a further aspect of the invention, the invention relates to the use of a compound of formula (I) in the preparation of a composition for coating a plant propagation material for the prevention or control of plant pathogenic fungi.

In a further aspect of the invention, the invention relates to a method of controlling or preventing infestation of plants or plant propagation material and/or harvested food crops susceptible to microbial attack by providing in a first step a agrochemical compositions according to the present invention comprising a compound of formula (I) and in a second step applying said composition to the plants or the locus thereof.

The compounds of formula (I) are applied by treating plant propagation material with a fungicidally effective amount of a compound of formula I. Preferably, compounds of formula (I) are applied by adhering compounds of formula (I) to plant propagation material in a fungicidally effective amount.

A preferred application method is seed treatment.

Where substituents are indicated as being optionally substituted, this means that they may or may not carry one or more identical or different substituents, e.g. one to three substituents. Normally not more than three such optional substituents are present at the same time. Where a group is indicated as being substituted, e.g. alkyl, this includes those groups that are part of other groups, e.g. the alkyl in alkoxy or phenyl in phenyloxy.

The number of substituents does not exceed the number of available C—H and N—H bonds, for example in the $C_1$-$C_4$alkoxy which can be substituted by one to five $R^5$ has only one to three substituents if methoxy is meant.

The term "halogen" refers to fluorine, chlorine, bromine or iodine, preferably fluorine, chlorine or bromine.

Alkyl substituents can be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl or iso-amyl.

Cycloalkyl includes cyclopropyl, cyclobutyl, cyclopentyl and cyclohexyl.

Alkenyl substituents can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Haloalkyl groups may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$.

Haloalkenyl groups are alkenyl groups, respectively, which are substituted with one or more of the same or different halogen atoms and are, for example, 2,2-difluorovinyl or 1,2-dichloro-2-fluoro-vinyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Haloalkoxy means a radical —OR, where R is haloalkyl, e.g. is described above. Haloalkloxy groups include, but are not limited to, $CH_2ClO$, $CHCl_2O$, $CCl_3O$, $CH_2FO$, $CHF_2O$—, $CF_3O$—, $CF_3CH_2O$—, $CH_3CF_2O$ or $CCl_3CCl_2O$—.

Cyano means a —CN group.

Amino means an —$NH_2$ group.

Hydroxyl or hydroxy stands for a —OH group.

Aryl means a ring system which can be mono-, bi- or tricyclic. Examples of such rings include phenyl, naphthalenyl, anthracenyl, indenyl or phenanthrenyl. A preferred aryl group is phenyl. Preferred optional substituents for aryl are halogen, cyano, hydroxyl, amino, nitro, $C_1$-$C_6$alkyl, $C_1$-$C_6$haloalkyl, $C_3$-$C_6$cycloalkyl, $C_3$-$C_6$halocycloalkyl, $C_1$-$C_6$alkoxy, $C_1$-$C_6$haloalkoxy, $C_3$-$C_6$cycloalkoxy, $C_1$-$C_6$alkylthio, $C_1$-$C_6$haloalkylthio, $C_3$-$C_6$cycloalkylthio, $C_1$-$C_6$alkylsulfinyl, $C_1$-$C_6$haloalkylsulfinyl, $C_3$-$C_6$cycloalkylsulfinyl, $C_1$-$C_6$alkylsulfonyl, $C_1C_6$haloalkylsulfonyl, $C_3$-$C_6$cycloalkylsulfonyl, $C_1$-$C_6$alkylcarbonyl, $C_2$-$C_6$alkenyl, $C_2$-$C_6$haloalkenyl, $C_2$-$C_6$alkenyloxy, $C_2$-$C_6$alkenylthio, $C_2$-$C_6$haloalkenyloxy, $C_2$-$C_6$alkynyl, $C_3$-$C_6$cycloalkyl $C_2$-$C_6$alkynyl, $C_2$-$C_6$alkynyloxy, $C_2$-$C_6$alkynyloxy, aryl, arylalkyl, aryloxy, arylthio, heteroaryl, heteroarylalkyl, heteroaryloxy and heteroarylthio, in which the aryl and heteroaryl groups are optionally substituted by one or more $R^5$.

Heteroaryl stands for aromatic heterocyclic ring systems, which can be mono-, bi- or tricyclic and wherein at least one oxygen, nitrogen or sulfur atom is present as a ring member, which can be accompanied by other oxygen, nitrogen, sulphur atoms as ring members. Monocyclic and bicyclic aromatic ring systems are preferred. For example, monocyclic heteroaryl can be a 5- or 6-membered ring containing one to three heteroatoms selected from oxygen, nitrogen and sulfur, more preferably selected from nitrogen and sulfur. Bicyclic heteroaryl can be a 9- or 10-membered bicyclic ring containing one to five heteroatoms, preferably one to three heteroatoms, selected from oxygen, nitrogen and sulfur. Examples of heteroaryl are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl. Heteroaryl rings do not contain adjacent oxygen ring atoms, adjacent sulfur ring atoms or adjacent oxygen and sulfur ring atoms. Preferred optional substituents for heteroaryl are halogen, cyano, hydroxyl, amino, nitro, $C_3$-$C_6$alkyl, $C_1$-$C_6$haloalkyl, $C_3$-$C_6$cycloalkyl, $C_3$-$C_6$halocycloalkyl, $C_1$-$C_6$alkoxy, $C_1$-$C_6$haloalkoxy, $C_3$-$C_6$cycloalkoxy, $C_1$-$C_6$alkylthio, $C_1$-$C_6$haloalkylthio, $C_3$-$C_6$cycloalkylthio, $C_1$-$C_6$alkylsulfinyl, $C_1$-$C_6$haloalkylsulfinyl, $C_3$-$C_6$cycloalkylsulfinyl, $C_1$-$C_6$alkylsulfonyl, $C_1$-$C_6$haloalkylsulfonyl, $C_3$-$C_6$cycloalkylsulfonyl, $C_1$-$C_6$alkylcarbonyl, $C_2$-$C_6$alkenyl, $C_2$-$C_6$haloalkenyl, $C_2$-$C_6$alkenyloxy, $C_2$-$C_6$alkenylthio, $C_2$-$C_6$haloalkenyloxy, $C_2$-$C_6$alkynyl, $C_3$-$C_6$cycloalkyl $C_2$-$C_6$alkynyl, $C_2$-$C_6$alkynyloxy, $C_2$-$C_6$alkynyloxy, aryl, arylalkyl, aryloxy, arylthio, heteroaryl, heteroarylalkyl, heteroaryloxy and heteroarylthio, in which the aryl and heteroaryl groups are optionally substituted by one or more $R^5$.

The presence of one or more possible asymmetric carbon atoms in a compound of formula (I) means that the compounds may occur in optically isomeric forms, i.e. enantiomeric or diastereomeric forms. Also atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

Suitable salts of the compounds, thus agronomically usable salts of compounds of formula (I) include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example killing, retardation, leaf burn, albinism, dwarfing and the like.

The term "insecticide" as used herein means a compound that controls or modifies the growth of insects. The term "insecticidally effective amount" means the quantity of such a compound or combination of such compounds that is capable of killing, controlling, or infecting insects, retarding the growth or reproduction of insects, reducing an insect population, and/or reducing damage to plants caused by insects.

The term "locus" as used herein means fields in or on which plants are growing, or where seeds of cultivated plants are sown, or where seed will be placed into the soil. It includes soil, seeds, and seedlings, as well as established vegetation.

The term "metabolism" as used herein means the conversion or breakdown of a substance from one form to another by a living organism.

The term "nematicide" as used herein means a compound that controls or modifies the growth of nematodes. The term "nematicidally effective amount" means the quantity of such a compound or combination of such compounds that is capable of killing, controlling, or infecting nematodes, retarding the growth or reproduction of nematodes, reducing a nematode population, and/or reducing damage to plants caused by nematodes.

A nematicidally effective amount" as used herein refers to an amount of nematicide capable of killing, controlling, or infecting nematodes, retarding the growth or reproduction of nematodes, reducing a nematode population, and/or reducing damage to plants caused by nematodes The term "plants" refers to all physical parts of a plant, including seeds, seedlings, saplings, roots, tubers, stems, stalks, foliage, and fruits.

The following list provides definitions, including preferred definitions, for substituents $R^1$, $R^2$, $R^3$, $R^4$, $R^5$, $R^{5a}$, $R^6$, $R^7$, X and Q with reference to compounds of formula (I). For any one of these substituents, any of the definitions given below can be combined with any definition of any other substituent given below or elsewhere in this document.

Preferably R$^a$ and R$^b$ independently are H, fluorine, chlorine, bromine, cyano, nitro, C$_1$-C$_4$alkyl, C$_1$-C$_4$alkoxy, C$_1$-C$_4$haloalkyl.

More preferably R$^a$ is fluorine, chlorine, bromine, cyano, nitro, C$_1$-C$_4$alkyl; and R$^b$ is H.

Even more preferably R$^a$ is fluorine, chlorine, bromine, cyano; and R$^b$ is H.

Most preferably R$^a$ is fluorine, chlorine; and R$^b$ is H.

In a further embodiment R$^a$ is H, fluorine, chlorine; and R$^b$ is H.

In more preferred compounds of formula (I) Q is selected from the group consisting of J-1 to J-59 (and π— represents the point of attachment of the heterocycle Q to the benzoxoborol moiety):

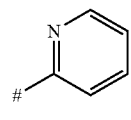
J-1

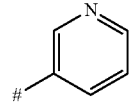
J-2

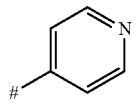
J-3

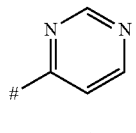
J-4

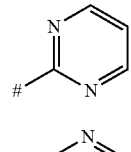
J-5

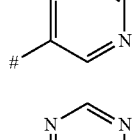
J-6

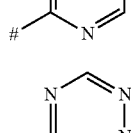
J-7

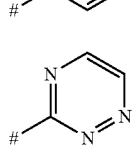
J-8

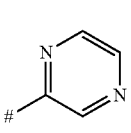
J-9

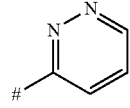
J-10

-continued

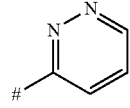
J-11

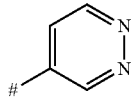
J-12

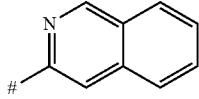
J-13

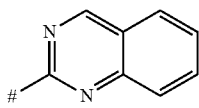
J-14

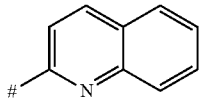
J-15

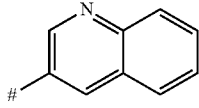
J-16

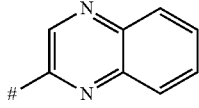
J-17

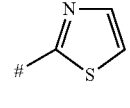
J-18

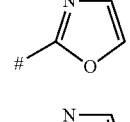
J-19

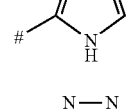
J-20

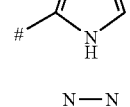
J-21

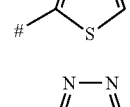
J-22

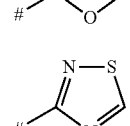
J-23

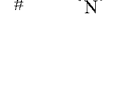
J-24

-continued
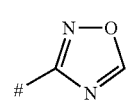 J-25
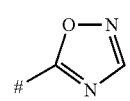 J-26
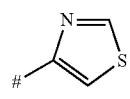 J-27
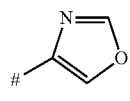 J-28
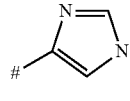 J-29
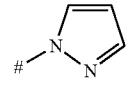 J-30
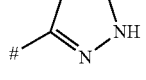 J-31
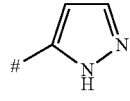 J-32
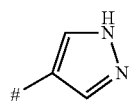 J-33
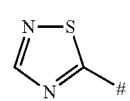 J-34
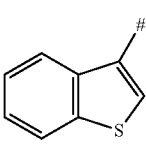 J-35
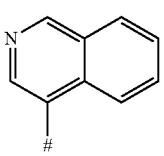 J-36
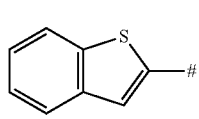 J-37
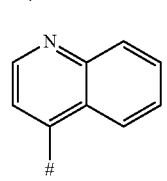 J-38
-continued
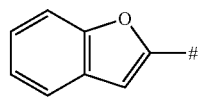 J-39
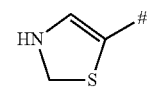 J-40
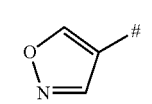 J-41
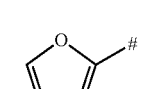 J-42
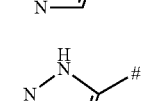 J-43
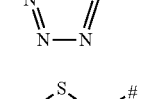 J-44
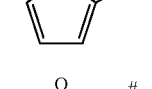 J-45
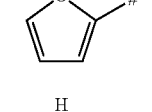 J-46
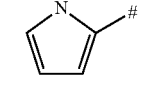 J-47
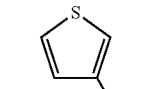 J-48
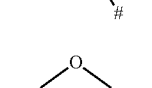 J-49
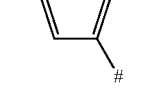 J-50
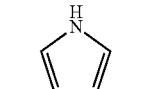 J-51
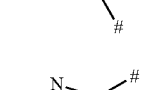
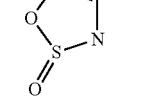
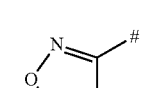

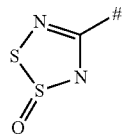
J-52

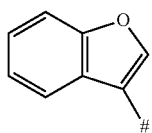
J-53

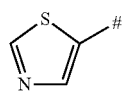
J-54

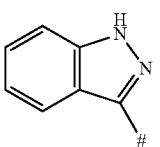
J-55

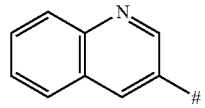
J-56

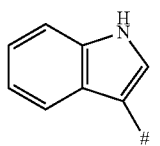
J-57

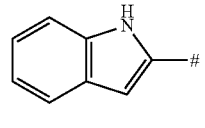
J-58

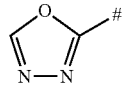
J-59 wherein each group J-1 to J-59 which can be substituted by one to five $R^5$.

In more preferred compounds of formula (I) Q is selected from the group consisting of J-1, J-2, J-3, J-10, J-18,19, J-23, J-25, J-26, J-27, J-32, J-33, J-37, J-39, J-41, J-42, J-43, J-44, J-45, J-46, J-47, J-48, J-53, J-54, J-55, J-56, J-57, J-58, and J-59.

In more preferred compounds of formula (I) Q is selected from the group consisting of J-2, J-3, J-6. J-18, J-19, J-26, J-31, J-32, J-37, J-38, J-41, J-42, J-43, J-44, J-45, J-46, and J-47 and each of the proups can substituted by one to five $R^5$.

In one embodiment Q is J-1 which can be substituted by one to five $R^5$ and $R^a$ and $R^b$ are selected as defined above. In one embodiment Q is J-2 which can be substituted by one to five $R^5$ and $R^a$ and $R^b$ are selected as defined above. In one embodiment Q is J-3 which can be substituted by one to five $R^5$ and $R^a$ and $R^b$ are selected as defined above. In one embodiment Q is J-4 which can be substituted by one to five $R^5$ and $R^a$ and $R^b$ are selected as defined above. In one embodiment Q is J-5 which can be substituted by one to five $R^5$ and $R^a$ and $R^b$ are selected as defined above. In one embodiment Q is J-6 which can be substituted by one to five $R^5$ and $R^a$ and $R^b$ are selected as defined above. In one embodiment Q is J-7 which can be substituted by one to five $R^5$ and $R^a$ and $R^b$ are selected as defined above. In one embodiment Q is J-8 which can be substituted by one to five $R^5$ and $R^a$ and $R^b$ are selected as defined above. In one embodiment Q is J-9 which can be substituted by one to five $R^5$ and $R^a$ and $R^b$ are selected as defined above. In one embodiment Q is J-10 which can be substituted by one to five $R^5$ and $R^a$ and $R^b$ are selected as defined above. In one embodiment Q is J-11 which can be substituted by one to five $R^5$ and $R^a$ and $R^b$ are selected as defined above. In one embodiment Q is J-12 which can be substituted by one to five $R^5$ and $R^a$ and $R^b$ are selected as defined above. In one embodiment Q is J-13 which can be substituted by one to five $R^5$ and $R^a$ and $R^b$ are selected as defined above. In one embodiment Q is J-14 which can be substituted by one to five $R^5$ and $R^a$ and $R^b$ are selected as defined above. In one embodiment Q is J-15 which can be substituted by one to five $R^5$ and $R^a$ and $R^b$ are selected as defined above. In one embodiment Q is J-16 which can be substituted by one to five $R^5$ and $R^a$ and $R^b$ are selected as defined above. In one embodiment Q is J-17 which can be substituted by one to five $R^5$ and $R^a$ and $R^b$ are selected as defined above. In one embodiment Q is J-18 which can be substituted by one to five $R^5$ and $R^a$ and $R^b$ are selected as defined above. In one embodiment Q is J-19 which can be substituted by one to five $R^5$ and $R^a$ and $R^b$ are selected as defined above. In one embodiment Q is J-20 which can be substituted by one to five $R^5$ and $R^a$ and $R^b$ are selected as defined above. In one embodiment Q is J-21 which can be substituted by one to five $R^5$ and $R^a$ and $R^b$ are selected as defined above. In one embodiment Q is J-22 which can be substituted by one to five $R^5$ and $R^a$ and $R^b$ are selected as defined above. In one embodiment Q is J-23 which can be substituted by one to five $R^5$ and $R^a$ and $R^b$ are selected as defined above. In one embodiment Q is J-24 which can be substituted by one to five $R^5$ and $R^a$ and $R^b$ are selected as defined above. In one embodiment Q is J-25 which can be substituted by one to five $R^5$ and $R^a$ and $R^b$ are selected as defined above. In one embodiment Q is J-26 which can be substituted by one to five $R^5$ and $R^a$ and $R^b$ are selected as defined above. In one embodiment Q is J-27 which can be substituted by one to five $R^5$ and $R^a$ and $R^b$ are selected as defined above. In one embodiment Q is J-28 which can be substituted by one to five $R^5$ and $R^a$ and $R^b$ are selected as defined above. In one embodiment Q is J-29 which can be substituted by one to five $R^5$ and $R^a$ and $R^b$ are selected as defined above. In one embodiment Q is J-30 which can be substituted by one to five $R^5$ and $R^a$ and $R^b$ are selected as defined above. In one embodiment Q is J-31 which can be substituted by one to five $R^5$ and $R^a$ and $R^b$ are selected as defined above. In one embodiment Q is J-32 which can be substituted by one to five $R^5$ and $R^a$ and $R^b$ are selected as defined above. In one embodiment Q is J-33 which can be substituted by one to five $R^5$ and $R^a$ and $R^b$ are selected as defined above. In one embodiment Q is J-34 which can be substituted by one to five $R^5$ and $R^a$ and $R^b$ are selected as defined above. In one embodiment Q is J-35 which can be substituted by one to five $R^5$ and $R^a$ and $R^b$ are selected as defined above. In one embodiment Q is J-36 which can be substituted by one to five $R^5$ and $R^a$ and $R^b$ are selected as defined above. In one embodiment Q is J-37 which can be substituted by one to five $R^5$ and $R^a$ and $R^b$ are selected as defined above. In one embodiment Q is J-38 which can be substituted by one to five $R^5$ and $R^a$ and $R^b$ are selected as defined above. In one embodiment Q is J-39 which can be substituted by one to five $R^5$ and $R^a$ and $R^b$ are selected as defined above. In one embodiment Q is J-40 which can be substituted by one to five $R^5$ and $R^a$ and $R^b$ are selected as defined above. In one embodiment Q is J-41 which can be substituted by one to five $R^5$ and $R^a$ and $R^b$ are selected as defined above. In one embodiment Q is J-42 which can be substituted by one to five $R^5$ and $R^a$ and $R^b$ are selected as defined above. In one embodiment Q is J-43 which can be substituted by one to five $R^5$ and $R^a$ and $R^b$ are selected as defined above. In one embodiment Q is J-44 which can be substituted by one to five $R^5$ and $R^a$ and $R^b$ are selected as defined above. In one embodiment Q is J-45 which can be substituted by one to five $R^5$ and $R^a$ and $R^b$ are selected as defined above. In one embodiment Q is J-46 which can be substituted by one to five $R^5$ and $R^a$ and $R^b$ are selected as defined above. In one embodiment Q is J-47 which can be substituted by one to five $R^5$ and $R^a$ and $R^b$ are selected as defined above. In one embodiment Q is J-48 which can be substituted by one to five $R^5$ and $R^a$ and $R^b$ are selected as defined above. In one embodiment Q is J-49 which can be substituted by one to five $R^5$ and $R^a$ and $R^b$ are selected as defined above. In one embodiment Q is J-50 which can be substituted by one to five $R^5$ and $R^a$ and $R^b$ are selected as defined above. In one embodiment Q is J-51 which can be substituted by one to five $R^5$ and $R^a$ and $R^b$ are selected as defined above. In one embodiment Q is J-52 which can be substituted by one to five $R^5$ and $R^a$ and $R^b$ are selected as defined above. In one embodiment Q is J-53 which can be substituted by one to five $R^5$ and $R^a$ and $R^b$ are selected as defined above. In one embodiment Q is J-54 which can be substituted by one to five $R^5$ and $R^a$ and $R^b$ are selected as defined above. In one embodiment Q is J-55 which can be substituted by one to five $R^5$ and $R^a$ and $R^b$ are selected as defined above. In one embodiment Q is J-56 which can be substituted by one to five $R^5$ and $R^a$ and $R^b$ are selected as defined above. In one embodiment Q is J-57 which can be substituted by one to five $R^5$ and $R^a$ and $R^b$ are selected as defined above. In one embodiment Q is J-58 which can be substituted by one to five $R^5$ and $R^a$ and $R^b$ are selected as defined above. In one embodiment Q is J-59 which can be substituted by one to five $R^5$ and $R^a$ and $R^b$ are selected as defined above.

In one embodiment $R^5$ selected from the group consisting of fluorine, chlorine, bromine, cyano, nitro, amino, hydroxyl, oxo, unsubstituted or substituted $C_1$-$C_6$alkyl, unsubstituted or substituted $C_1$-$C_6$haloalkyl, unsubstituted or substituted $C_3$-$C_5$cycloalky, unsubstituted or substituted $C_2$-$C_6$alkenyl, unsubstituted or substituted $C_2$-$C_6$alkynyl, unsubstituted or substituted $C_1$-$C_6$alkoxy, unsubstituted or substituted $C_1$-$C_6$haloalkoxy, unsubstituted or substituted $C_1$-$C_6$alkylthio, wherein the substituents are selected from halogen, —$NR^6R^7$, $C_1$-$C_4$alkyl, $C_1$-$C_4$haloalkyl, $C_1$-$C_4$alkoxy, —CN, —$NO_2$.

In a further embodiment $R^5$ selected from the group consisting of —C(O)H, —C(O)($C_{1-4}$alkoxy), —C(O)($C_{1-4}$alkyl), —C(O)—NH—($C_{1-4}$alkyl), —C(O)—N($C_{1-4}$alkyl)$_2$, $C_1$-$C_4$alkyl, $C_1$-$C_4$haloalkyl, $C_1$-$C_4$alkoxy, $C_1$-$C_4$alkylthio, $C_1$-$C_4$alkoxy-$C_1$-$C_4$alkyl, $C_1$-$C_4$haloalkoxy, hydroxyimino, $C_1$-$C_4$alkoximino, $C_1$-$C_4$alkoximino $C_1$-$C_4$alkyl and $C_1$-$C_4$alkylendioxy; —C(O)NH($C_{1-4}$alkyl), —C(O)N($C_{1-4}$alkyl)($C_{1-4}$alkyl), —OC(O)NH($C_{1-4}$alkyl), —OC(O)N($C_{1-4}$alkyl)($C_{1-4}$alkyl), —NHC(O)($C_{1-4}$alkyl), —NHC(O)($C_{1-4}$alkoxy), —N($C_{1-4}$alkyl)C(O)($C_{1-4}$alkyl), —N($C_{1-4}$alkyl)C(O)($C_{1-4}$alkoxy), —OC(O) ($C_{1-4}$alkyl), —C(=N—O—($C_{1-4}$alkyl)-H, —C(=N—O—($C_{1-4}$alkyl)-$C_1$-$C_4$alkyl;

In a further embodiment $R^5$ independently selected from the group consisting of a —X-(6 to 10 membered-aryl) group which is can be substituted by halogen, $C_1$-$C_4$alkyl, $C_1$-$C_4$haloalkyl, $C_1$-$C_4$alkoxy, —CN, —$NO_2$, In a further embodiment $R^5$ independently selected from the group consisting of -X-linked-5- or 6-membered heteroaryl group which comprises one or two or three heteroatoms selected from or two N, O and S which can be substituted by halogen, $C_1$-$C_4$alkyl, $C_1$-$C_4$haloalkyl, $C_1$-$C_4$alkoxy, —CN, —$NO_2$, —$NR^6R^7$, $C_3$-$C_6$cycloalkyl, In a further embodiment $R^5$ independently selected from the group consisting of fluorine, chlorine, bromine, cyano, nitro, amino, hydroxyl, oxo, $C_1$-$C_6$alkyl, $C_1$-$C_6$haloalkyl, $C_3$-$C_5$cycloalky, $C_2$-$C_6$alkenyl, $C_2$-$C_6$alkynyl, $C_1$-$C_6$alkoxy, unsubstituted or substituted $C_1$-$C_6$haloalkoxy, $C_1$-$C_6$alkylthio, —C(O)H, —C(O)($C_{1-4}$alkoxy), —C(O)($C_{1-4}$alkyl), hydroxyimino, $C_1$-$C_4$alkoximino, $C_1$-$C_4$alkoximino $C_1$-$C_4$alkyl;

In a further embodiment $R^5$ independently selected from a -X-linked-5- or 6-membered heterocycloalkyl group which comprises one or two or three heteroatoms selected from or two N, O and S which can be substituted by one to five substituents selected from can be substituted by halogen, $C_1$-$C_4$alkyl, $C_1$-$C_4$haloalkyl, $C_1$-$C_4$alkoxy, —CN, —$NO_2$, —$NR^6R^7$, $C_3$-$C_6$cycloalkyl;

In a preferred embodiment $R^5$ independently selected from the group consisting of chlorine, cyano, hydroxyl, $C_1$-$C_6$alkyl, $C_1$-$C_6$alkylthio, —C(O)H, —C(O)($C_{1-4}$alkyl), hydroxyimino, $C_1$-$C_4$alkoximino $C_1$-$C_4$alkoximino $C_1$-$C_4$alkyl, N-morpholine.

The invention further relates to a compound according to the formula (VIII)

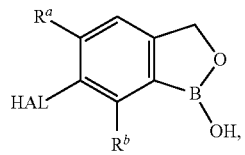

(VIII)

Wherein
HAL is halogen;
and $R^a$ and $R^b$ independently are H, fluorine, chlorine, bromine, cyano, nitro, $C_1$-$C_4$alkyl, $C_1$-$C_4$alkoxy, $C_1$-$C_4$haloalkyl;
preferably HAL is fluorine, chlorine, bromine or idodine;
more preferably preferably HAL is idodine;
Preferably $R^a$ is fluorine, chlorine, bromine, cyano, nitro, $C_1$-$C_4$alkyl; and $R^b$ is H.
More preferably $R^a$ is fluorine, chlorine, bromine, cyano; and $R^b$ is H.
Most preferably $R^a$ is fluorine, chlorine; and $R^b$ is H.
In a preferred embodiment the compound according to the formula (I-A) is characterized in that HAL is iodine;
and $R^a$ and $R^b$ independently are H, fluorine, chlorine, bromine, cyano, nitro, $C_1$-$C_4$alkyl, $C_1$-$C_4$alkoxy, $C_1$-$C_4$haloalkyl;
preferably HAL is fluorine, chlorine, bromine or idodine;
more preferably HAL is idodine;
Preferably $R^a$ is fluorine, chlorine, bromine, cyano, nitro, $C_1$-$C_4$alkyl; and $R^b$ is H.
More preferably $R^a$ is fluorine, chlorine, bromine, cyano; and $R^b$ is H.
Most preferably $R^a$ is fluorine, chlorine; and $R^b$ is H.
The invention further relates to a compound according to the formula (I-A)

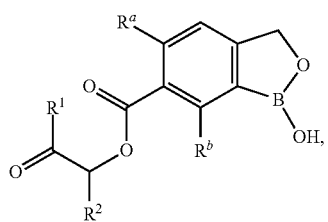

(I-A)

Wherein
R$^1$ and R$^2$ independently are C$_1$-C$_4$alkyl, C$_1$-C$_4$haloalkyl, phenyl;
and R$^a$ and R$^b$ independently are H, fluorine, chlorine, bromine, cyano, nitro, C$_1$-C$_4$alkyl, C$_1$-C$_4$alkoxy, C$_1$-C$_4$haloalkyl;
preferably R$^1$ and R$^2$ independently are C$_1$-C$_4$alkyl;
more preferably R$^1$ and R$^2$ are both methyl.
Preferably R$^a$ is fluorine, chlorine, bromine, cyano, nitro, C$_1$-C$_4$alkyl; and R$^b$ is H.
More preferably R$^a$ is fluorine, chlorine, bromine, cyano; and R$^b$ is H.
Most preferably R$^a$ is fluorine, chlorine; and R$^b$ is H.
The invention further relates to a compound according to the formula (I-B)

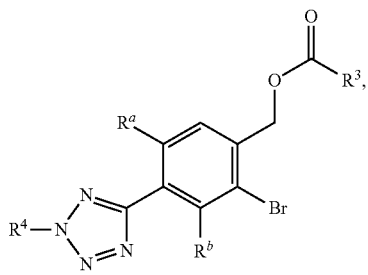

(I-B)

Wherein
R$^3$ and R$^4$ independently are C$_1$-C$_4$alkyl, C$_1$-C$_4$haloalkyl, phenyl;
preferably R$^1$ and R$^2$ independently are C$_1$-C$_4$alkyl;
more preferably R$^1$ and R$^2$ are both methyl;
and R$^a$ and R$^b$ independently are H, fluorine, chlorine, bromine, cyano, nitro, C$_1$-C$_4$alkyl, C$_1$-C$_4$alkoxy, C$_1$-C$_4$haloalkyl;
Preferably R$^a$ is fluorine, chlorine, bromine, cyano, nitro, C$_1$-C$_4$alkyl; and R$^b$ is H.
More preferably R$^a$ is fluorine, chlorine, bromine, cyano; and R$^b$ is H.
Most preferably R$^a$ is fluorine, chlorine; and R$^b$ is H.
The invention further relates to a compound according to the formula (I-C)

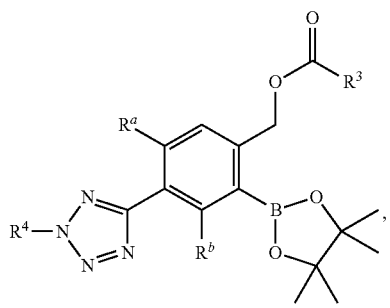

(I-C)

Wherein
R$^3$ and R$^4$ independently are C$_1$-C$_4$alkyl, C$_1$-C$_4$haloalkyl, phenyl;
preferably R$^1$ and R$^2$ independently are C$_1$-C$_4$alkyl;
more preferably preferably R$^1$ and R$^2$ are both methyl;
and R$^a$ and R$^b$ independently are H, fluorine, chlorine, bromine, cyano, nitro, C$_1$-C$_4$alkyl, C$_1$-C$_4$haloalkyl;
Preferably R$^a$ is fluorine, chlorine, bromine, cyano, nitro, C$_1$-C$_4$alkyl; and R$^b$ is H.
More preferably R$^a$ is fluorine, chlorine, bromine, cyano; and R$^b$ is H.
Most preferably R$^a$ is fluorine, chlorine; and R$^b$ is H.
The invention further relates to a compound according to the formula (I-D)

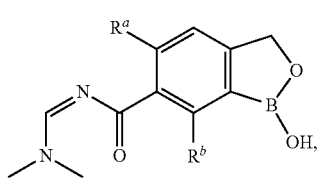

(I-D)

Wherein
and R$^a$ and R$^b$ independently are H, fluorine, chlorine, bromine, cyano, nitro, C$_1$-C$_4$alkyl, C$_1$-C$_4$alkoxy, C$_1$-C$_4$haloalkyl;
Preferably R$^a$ is fluorine, chlorine, bromine, cyano, nitro, C$_1$-C$_4$alkyl; and R$^b$ is H.
More preferably R$^a$ is fluorine, chlorine, bromine, cyano; and R$^b$ is H.
Most preferably R$^a$ is fluorine, chlorine; and R$^b$ is H.
The invention further relates to a compound according to the formula (I-E)
Wherein

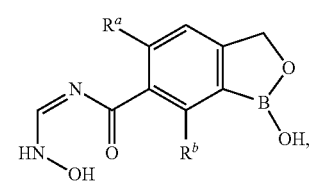

(I-E)

and R$^a$ and R$^b$ independently are H, fluorine, chlorine, bromine, cyano, nitro, C$_1$-C$_4$alkyl, C$_1$-C$_4$alkoxy, C$_4$haloalkyl;
Preferably R$^a$ is fluorine, chlorine, bromine, cyano, nitro, C$_1$-C$_4$alkyl; and R$^b$ is H.
More preferably R$^a$ is fluorine, chlorine, bromine, cyano; and R$^b$ is H.
Most preferably R$^a$ is fluorine, chlorine; and R$^b$ is H.
The following tables 1 to 81 illustrate further compounds according to the invention
Table 1
Table 1 provides 59 compounds of formula (I) wherein R$^a$ is methyl, R$^b$ is methyl, and Q is defined in Table P.
Table 2
Table 2 provides 59 compounds of formula (I) wherein R$^a$ is ethyl, R$^b$ is methyl, and Q is defined in Table P.
Table 3
Table 3 provides 59 compounds of formula (I) wherein R$^a$ is F, R$^b$ is methyl, and Q is defined in Table P.

Table 4
Table 4 provides 59 compounds of formula (I) wherein $R^a$ is Cl, $R^b$ is methyl, and Q is defined in Table P.
Table 5
Table 5 provides 59 compounds of formula (I) wherein $R^a$ is Br, $R^b$ is methyl, and Q is defined in Table P.
Table 6
Table 6 provides 59 compounds of formula (I) wherein $R^a$ is CN, $R^b$ is methyl, and Q is defined in Table P.
Table 7
Table 7 provides 59 compounds of formula (I) wherein $R^a$ is methoxy, $R^b$ is methyl, and Q is defined in Table P.
Table 8
Table 8 provides 59 compounds of formula (I) wherein $R^a$ is ethoxy, $R^b$ is methyl, and Q is defined in Table P.
Table 9
Table 9 provides 59 compounds of formula (I) wherein $R^a$ is H, $R^b$ is methyl, and Q is defined in Table P.
Table 10
Table 10 provides 59 compounds of formula (I) wherein $R^a$ is methyl, $R^b$ is ethyl, and Q is defined in Table P.
Table 11
Table 11 provides 59 compounds of formula (I) wherein $R^a$ is ethyl, $R^b$ is ethyl, and Q is defined in Table P.
Table 12
Table 12 provides 59 compounds of formula (I) wherein $R^a$ is F, $R^b$ is ethyl, and Q is defined in Table P.
Table 13
Table 13 provides 59 compounds of formula (I) wherein $R^a$ is Cl, $R^b$ is ethyl, and Q is defined in Table P.
Table 14
Table 14 provides 59 compounds of formula (I) wherein $R^a$ is Br, $R^b$ is ethyl, and Q is defined in Table P.
Table 15
Table 15 provides 59 compounds of formula (I) wherein $R^a$ is CN, $R^b$ is ethyl, and Q is defined in Table P.
Table 16
Table 16 provides 59 compounds of formula (I) wherein $R^a$ is methoxy, $R^b$ is ethyl, and Q is defined in Table P.
Table 17
Table 17 provides 59 compounds of formula (I) wherein $R^a$ is ethoxy, $R^b$ is ethyl, and Q is defined in Table P.
Table 18
Table 18 provides 59 compounds of formula (I) wherein $R^a$ is H, $R^b$ is ethyl, and Q is defined in Table P.
Table 19
Table 19 provides 59 compounds of formula (I) wherein $R^a$ is methyl, $R^b$ is F, and Q is defined in Table P.
Table 20
Table 20 provides 59 compounds of formula (I) wherein $R^a$ is ethyl, $R^b$ is F, and Q is defined in Table P.
Table 21
Table 21 provides 59 compounds of formula (I) wherein $R^a$ is F, $R^b$ is F, and Q is defined in Table P.
Table 22
Table 22 provides 59 compounds of formula (I) wherein $R^a$ is Cl, $R^b$ is F, and Q is defined in Table P.
Table 23
Table 23 provides 59 compounds of formula (I) wherein $R^a$ is Br, $R^b$ is F, and Q is defined in Table P.
Table 24
Table 24 provides 59 compounds of formula (I) wherein $R^a$ is CN, $R^b$ is F, and Q is defined in Table P.
Table 25
Table 25 provides 59 compounds of formula (I) wherein $R^a$ is methoxy, $R^b$ is F, and Q is defined in Table P.
Table 26
Table 26 provides 59 compounds of formula (I) wherein $R^a$ is ethoxy, $R^b$ is F, and Q is defined in Table P.
Table 27
Table 27 provides 59 compounds of formula (I) wherein $R^a$ is H, $R^b$ is F, and Q is defined in Table P.
Table 28
Table 28 provides 59 compounds of formula (I) wherein $R^a$ is methyl, $R^b$ is Cl, and Q is defined in Table P.
Table 29
Table 29 provides 59 compounds of formula (I) wherein $R^a$ is ethyl, $R^b$ is Cl, and Q is defined in Table P.
Table 30
Table 30 provides 59 compounds of formula (I) wherein $R^a$ is F, $R^b$ is Cl, and Q is defined in Table P.
Table 31
Table 31 provides 59 compounds of formula (I) wherein $R^a$ is Cl, $R^b$ is Cl, and Q is defined in Table P.
Table 32
Table 32 provides 59 compounds of formula (I) wherein $R^a$ is Br, $R^b$ is Cl, and Q is defined in Table P.
Table 33
Table 33 provides 59 compounds of formula (I) wherein $R^a$ is CN, $R^b$ is Cl, and Q is defined in Table P.
Table 34
Table 34 provides 59 compounds of formula (I) wherein $R^a$ is methoxy, $R^b$ is Cl, and Q is defined in Table P.
Table 35
Table 35 provides 59 compounds of formula (I) wherein $R^a$ is ethoxy, $R^b$ is Cl, and Q is defined in Table P.
Table 36
Table 36 provides 59 compounds of formula (I) wherein $R^a$ is H, $R^b$ is Cl, and Q is defined in Table P.
Table 37
Table 37 provides 59 compounds of formula (I) wherein $R^a$ is methyl, $R^b$ is Br, and Q is defined in Table P.
Table 38
Table 38 provides 59 compounds of formula (I) wherein $R^a$ is ethyl, $R^b$ is Br, and Q is defined in Table P.
Table 39
Table 39 provides 59 compounds of formula (I) wherein $R^a$ is F, $R^b$ is Br, and Q is defined in Table P.
Table 40
Table 40 provides 59 compounds of formula (I) wherein $R^a$ is Cl, $R^b$ is Br, and Q is defined in Table P.
Table 41
Table 41 provides 59 compounds of formula (I) wherein $R^a$ is Br, $R^b$ is Br, and Q is defined in Table P.
Table 42
Table 42 provides 59 compounds of formula (I) wherein $R^a$ is CN, $R^b$ is Br, and Q is defined in Table P.
Table 43
Table 43 provides 59 compounds of formula (I) wherein $R^a$ is methoxy, $R^b$ is Br, and Q is defined in Table P.
Table 44
Table 44 provides 59 compounds of formula (I) wherein $R^a$ is ethoxy, $R^b$ is Br, and Q is defined in Table P.
Table 45
Table 45 provides 59 compounds of formula (I) wherein $R^a$ is H, $R^b$ is Br, and Q is defined in Table P.
Table 46
Table 46 provides 59 compounds of formula (I) wherein $R^a$ is methyl, $R^b$ is CN, and Q is defined in Table P.
Table 47
Table 47 provides 59 compounds of formula (I) wherein $R^a$ is ethyl, $R^b$ is CN, and Q is defined in Table P.

Table 48

Table 48 provides 59 compounds of formula (I) wherein $R^a$ is F, $R^b$ is CN, and Q is defined in Table P.

Table 49

Table 49 provides 59 compounds of formula (I) wherein $R^a$ is Cl, $R^b$ is CN, and Q is defined in Table P.

Table 50

Table 50 provides 59 compounds of formula (I) wherein $R^a$ is Br, $R^b$ is CN, and Q is defined in Table P.

Table 51

Table 51 provides 59 compounds of formula (I) wherein $R^a$ is CN, $R^b$ is CN, and Q is defined in Table P.

Table 52

Table 52 provides 59 compounds of formula (I) wherein $R^a$ is methoxy, $R^b$ is CN, and Q is defined in Table P.

Table 53

Table 53 provides 59 compounds of formula (I) wherein $R^a$ is ethoxy, $R^b$ is CN, and Q is defined in Table P.

Table 54

Table 54 provides 59 compounds of formula (I) wherein $R^a$ is H, $R^b$ is CN, and Q is defined in Table P.

Table 55

Table 55 provides 59 compounds of formula (I) wherein $R^a$ is methyl, $R^b$ is methoxy, and Q is defined in Table P.

Table 56

Table 56 provides 59 compounds of formula (I) wherein $R^a$ is ethyl, $R^b$ is methoxy, and Q is defined in Table P.

Table 57

Table 57 provides 59 compounds of formula (I) wherein $R^a$ is F, $R^b$ is methoxy, and Q is defined in Table P.

Table 58

Table 58 provides 59 compounds of formula (I) wherein $R^a$ is Cl, $R^b$ is methoxy, and Q is defined in Table P.

Table 59

Table 59 provides 59 compounds of formula (I) wherein $R^a$ is Br, $R^b$ is methoxy, and Q is defined in Table P.

Table 60

Table 60 provides 59 compounds of formula (I) wherein $R^a$ is CN, $R^b$ is methoxy, and Q is defined in Table P.

Table 61

Table 61 provides 59 compounds of formula (I) wherein $R^a$ is methoxy, $R^b$ is methoxy, and Q is defined in Table P.

Table 62

Table 62 provides 59 compounds of formula (I) wherein $R^a$ is ethoxy, $R^b$ is methoxy, and Q is defined in Table P.

Table 63

Table 63 provides 59 compounds of formula (I) wherein $R^a$ is H, $R^b$ is methoxy, and Q is defined in Table P.

Table 64

Table 64 provides 59 compounds of formula (I) wherein $R^a$ is methyl, $R^b$ is ethoxy, and Q is defined in Table P.

Table 65

Table 65 provides 59 compounds of formula (I) wherein $R^a$ is ethyl, $R^b$ is ethoxy, and Q is defined in Table P.

Table 66

Table 66 provides 59 compounds of formula (I) wherein $R^a$ is F, $R^b$ is ethoxy, and Q is defined in Table P.

Table 67

Table 67 provides 59 compounds of formula (I) wherein $R^a$ is Cl, $R^b$ is ethoxy, and Q is defined in Table P.

Table 68

Table 68 provides 59 compounds of formula (I) wherein $R^a$ is Br, $R^b$ is ethoxy, and Q is defined in Table P.

Table 69

Table 69 provides 59 compounds of formula (I) wherein $R^a$ is CN, $R^b$ is ethoxy, and Q is defined in Table P.

Table 70

Table 70 provides 59 compounds of formula (I) wherein $R^a$ is methoxy, $R^b$ is ethoxy, and Q is defined in Table P.

Table 71

Table 71 provides 59 compounds of formula (I) wherein $R^a$ is ethoxy, $R^b$ is ethoxy, and Q is defined in Table P.

Table 72

Table 72 provides 59 compounds of formula (I) wherein $R^a$ is H, $R^b$ is ethoxy, and Q is defined in Table P.

Table 73

Table 73 provides 59 compounds of formula (I) wherein $R^a$ is methyl, $R^b$ is H, and Q is defined in Table P.

Table 74

Table 74 provides 59 compounds of formula (I) wherein $R^a$ is ethyl, $R^b$ is H, and Q is defined in Table P.

Table 75

Table 75 provides 59 compounds of formula (I) wherein $R^a$ is F, $R^b$ is H, and Q is defined in Table P.

Table 76

Table 76 provides 59 compounds of formula (I) wherein $R^a$ is Cl, $R^b$ is H, and Q is defined in Table P.

Table 77

Table 77 provides 59 compounds of formula (I) wherein $R^a$ is Br, $R^b$ is H, and Q is defined in Table P.

Table 78

Table 78 provides 59 compounds of formula (I) wherein $R^a$ is CN, $R^b$ is H, and Q is defined in Table P.

Table 79

Table 79 provides 59 compounds of formula (I) wherein $R^a$ is methoxy, $R^b$ is H, and Q is defined in Table P.

Table 80

Table 80 provides 59 compounds of formula (I) wherein $R^a$ is ethoxy, $R^b$ is H, and Q is defined in Table P.

Table 81

Table 81 provides 59 compounds of formula (I) wherein $R^a$ is H, $R^b$ is H, and Q is defined in Table P.

TABLE P

| Entry | Q |
|---|---|
| 1 | J-1 |
| 2 | J-2 |
| 3 | J-3 |
| 4 | J-4 |
| 5 | J-5 |
| 6 | J-6 |
| 7 | J-7 |
| 8 | J-8 |
| 9 | J-9 |
| 10 | J-10 |
| 11 | J-11 |
| 12 | J-12 |
| 13 | J-13 |
| 14 | J-14 |
| 15 | J-15 |
| 16 | J-16 |
| 17 | J-17 |
| 18 | J-18 |
| 19 | J-19 |
| 20 | J-20 |
| 21 | J-21 |
| 22 | J-22 |
| 23 | J-23 |
| 24 | J-24 |
| 25 | J-25 |
| 26 | J-26 |
| 27 | J-27 |
| 28 | J-28 |
| 29 | J-29 |
| 30 | J-30 |
| 31 | J-31 |
| 32 | J-32 |
| 33 | J-33 |

TABLE P-continued

| Entry | Q |
|---|---|
| 34 | J-34 |
| 35 | J-35 |
| 36 | J-36 |
| 37 | J-37 |
| 38 | J-38 |
| 39 | J-39 |
| 40 | J-40 |
| 41 | J-41 |
| 42 | J-42 |
| 43 | J-43 |
| 44 | J-44 |
| 45 | J-45 |
| 46 | J-46 |
| 47 | J-47 |
| 48 | J-48 |
| 49 | J-49 |
| 50 | J-50 |
| 51 | J-51 |
| 52 | J-52 |
| 53 | J-53 |
| 54 | J-54 |
| 55 | J-55 |
| 56 | J-56 |
| 57 | J-57 |
| 58 | J-58 |
| 59 | J-59 |

Compounds described in the present invention can be prepared using commercially available starting materials or known intermediates using synthetic methods known in the art or described herein. The following general chemistry routes were used as indicated in generating the examples and can be applied, using the knowledge of one of skill in the art, to other appropriate compounds to obtain additional analogues The compounds of formula (I)

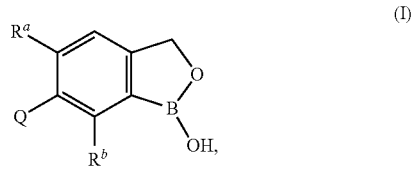

(I)

may be prepared by reacting a compound of formula II with a compound of formula III

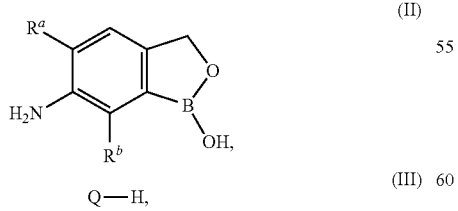

wherein Q, $R^a$ and $R^b$ are as defined under formula I.

The compounds of formula (I) and the respective starting materials may be obtained according to the processes of Schemes 1 to 5.

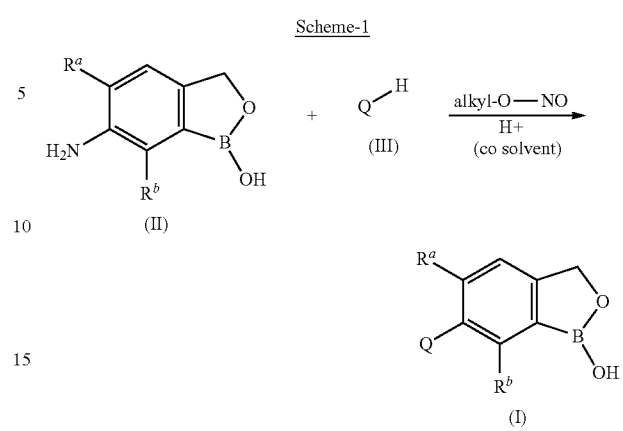

Some compounds of formula (III) are known and commercially available. The reaction for the preparation of compounds of formula (I) according scheme-1 is advantageously carried out directly in liquid compounds of formula (III) without co-solvents. If compounds of formula (III) are solids, the reactions for preparation of compounds of formula (I) are carried out in solvents. Such solvents are alcohols such as methanol, ethanol, n-propanol, i-propanol, nitriles, such as acetonitrile, propionitrile chlorinated hydrocarbons such as dichloromethane, trichloromethane, tetrachloromethane ethers such as diethyl ether, ethylene glycol dimethyl ether, diethylene glycol dimethyl ether, tetrahydrofuran or dioxane amides such as N,N-dimethylformamide, diethylformamide or N-methylpyrrolidinone. Alkylnitrites are preferably ethyl nitrite, n-Butyl nitrite tert-butyl nitrite, amyl nitrite, isoamyl nitrite. The reaction temperatures are advantageously between 0° C. and 60° C. The reaction times can be shortened by adding a few drops of acids as reaction catalyst. Suitable acids are, in particular, trifluoroacetic acid, HBr and HCl.

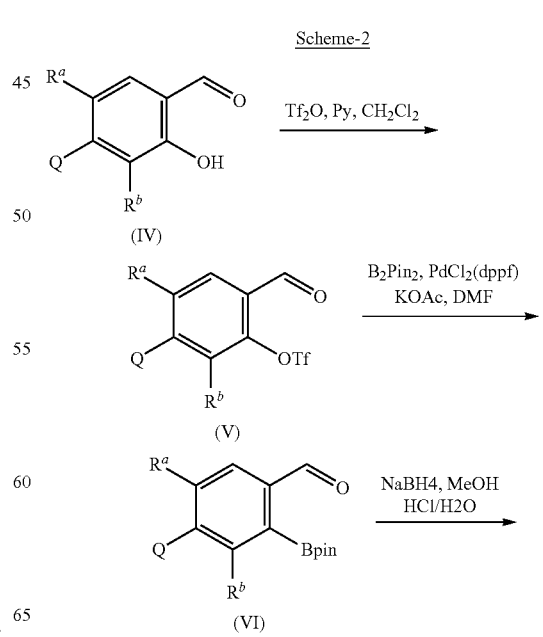

-continued

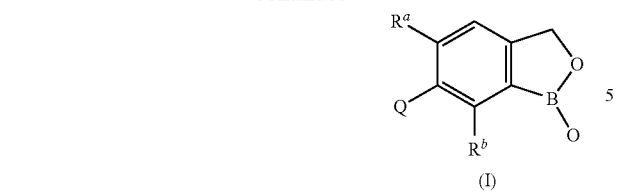
(I)

Scheme-3

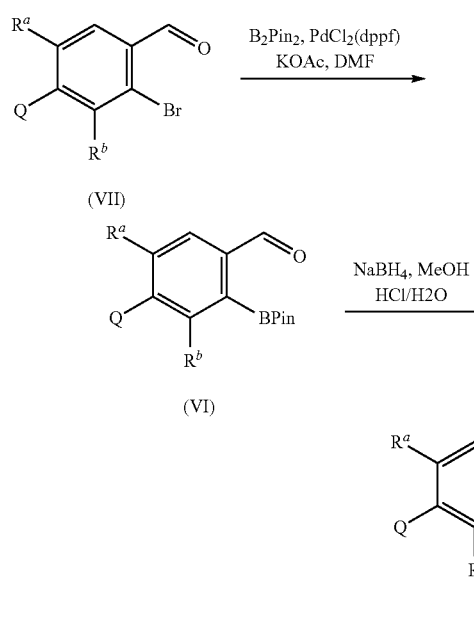

Compounds of formula IV and VII are either commercially available or can be prepared by those skilled in the art with a number of different conditions already known.

Scheme-4

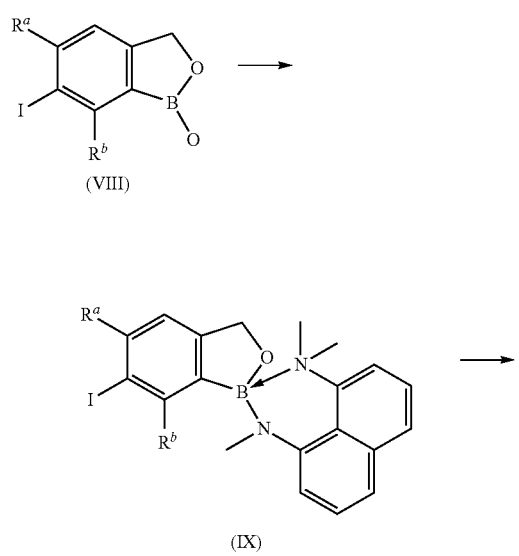

-continued

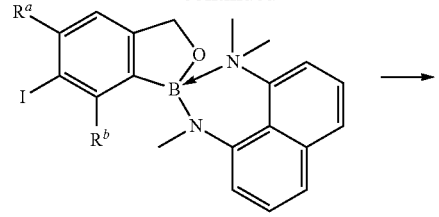
(X)

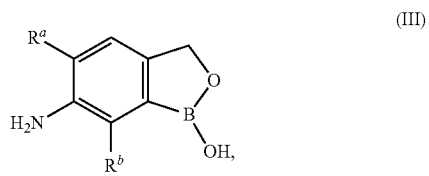
(I)

Compounds of formula (IX) may be made in analogy to known methods published in RSC Adv., 2013, 3, 21331-2133. Intermediates of formula (IX) can undergo Suzuki coupling reaction to form compound of formula (X) as described in reaction scheme 4. It will be appreciated by those skilled in the art that this coupling reaction can be carried out with a number of different conditions. Intermediate of formula (X) can be deprotected using acidic conditions to obtain compounds of formula (I). Suitable acids are, in particular, trifluoroacetic acid, HBr and HCl.

The intermediates of formula III (III)

wherein $R^a$ and $R^b$ is defined under formula I, preferably wherein $R^a$ is F and $R^b$ is H (CAS Registry Number: 943311-50-0), $R^a$ is Cl, $R^b$ is H (CAS Registry Number: 947165-43-7), are known, and described in the literature, for example in Bioorganic & Medicinal Chemistry Letters, 20(24), 7317-7322; 2010, or Journal of Molecular Biology, 390(2), 196-207; 2009 or Bioorganic & Medicinal Chemistry Letters, 21(7), 2048-2054; 2011.

The compounds of formula (I) of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound.

Compounds of formula (I) and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

They are effective in controlling a broad spectrum of plant diseases, such as foliar pathogens of ornamental, turf, vegetable, field, cereal, and fruit crops.

These pathogens may include:

Oomycetes, including Phytophthora diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica;* Pythium diseases such as those caused by *Pythium aphanidermaturn, Pythium arrhenomanes, Pythium graminicola, Pythium irregulare* and *Pythium ultimum;* diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae;* and others such as *Aphanomyces cochlioides, Labyrinthula zosterae, Peronosclerospora sorghi* and *Sclerospora graminicola.*

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructiva, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum, Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani* and *Alternaria tomatophila,* Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collo-cygni,* Magnaporthales such as *Gaeumannomyces graminis, Magnaporthe grisea, Pyricularia oryzae,* Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma,* and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petriellidium* spp., *Pezicula* spp. *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor, Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis;* powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata and Oidium arachidis;* molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum;* anthracnoses for example those caused by Glommerelales such as *Colletotrichum gloeosporioides, Colletotrichum lagenarium, Colletotrichum gossypii, Glomerella cingulata,* and *Colletotrichum graminicola;* and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f.sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum,* and *Verticillium theobromae.*

Basidiomycetes, including smuts for example those caused by Ustilaginales such as *Ustilaginoidea virens, Ustilago nuda, Ustilago tritici, Ustilago zeae,* rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f.sp. Hordei, *Puccinia striiformis* f.sp. Secalis, *Pucciniastrum coryli,* or Uredinales such as *Cronartium ribicola, Gymnosporangium juniperi-virginianae, Melampsora medusae, Phakopsora pachyrhizi, Phragmidium mucronatum, Physopella ampelosidis, Tranzschelia discolor* and *Uromyces viciae-fabae;* and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisaria fuciformis, Waitea circinata, Rhizoctonia solani, Thanetephorus cucurmeris, Entyloma dahliae, Entylomella microspora, Neovossia moliniae* and *Tilletia caries.*

Blastocladiomycetes, such as *Physoderma maydis.*

Mucoromycetes, such as *Choanephora cucurbitarum.; Mucor* spp.; *Rhizopus arrhizus.*

As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Strptomyces scabies* and other related species as well as certain protozoa.

Compounds of formula (I) may be mixed with one or more of compounds selected from those in the following chemical or functional classes: 1,2,4-thiadiazoles, 2,6-dinitroanilines, acylalanines, aliphatic nitrogenous compounds, amidines, aminopyrimidinols, anilides, anilino-pyrimidines, anthraquinones, antibiotics, aryl-phenylketones, benzamides, benzene-sulfonamides, benzimidazoles, benzothiazoles, benzothiodiazoles, benzothiophenes, benzoylpyridines, benzthiadiazoles, benzylcarbamates, butylamines, carbamates, carboxamides, carpropamids, chloronitriles, cinnamic acid amides, copper containing compounds, cyanoacetamideoximes, cyanoacrylates, cyanoimidazoles, cyanomethylene-thiazolidines, dicarbonitriles, dicarboxamides, dicarboximides, dimethylsulphamates, dinitrophenol carbonates, dinitrophenysl, dinitrophenyl crotonates, diphenyl phosphates, dithiino compounds, dithiocarbamates, dithioethers, dithiolanes, ethyl-amino-thiazole carboxamides, ethyl-phosphonates, furan carboxamides, glucopyranosyls, glucopyranoxyls, glutaronitriles, guanidines, herbicides/plant growth regulatosr, hexopyranosyl antibiotics, hydroxy(2-amino)pyrimidines, hydroxyanilides, hydroxyisoxazoles, imidazoles, imidazolinones, insecticides/plant growth regulators, isobenzofuranones, isoxazolidinyl-pyridines, isoxazolines, maleimides, mandelic acid amides, mectin derivatives, morpholines, norpholines, n-phenyl carbamates, organotin compounds, oxathiin carboxamides, oxazoles, oxazolidine-diones, phenols, phenoxy quinolines, phenylacetamides, phenylamides, phenylbenzamides, phenyl-oxoethyl-thiophenes amides, phenylpyrroles, phenylureas, phosphorothiolates, phosphorus acids, phthalamic acids, phthalimides, picolinamides, piperazines, piperidines, plant extracts, polyoxins, propionamides, pthalimides, pyrazole-4-carboxamides, pyrazolinones, pyridazinones, pyridines, pyridine carboxamides, pyridinyl-ethyl benzamides, pyrimdinamines, pyrimidines, pyrimidine-amines, pyrimidionehydrazone, pyrrolidines, pyrrolquinoliones, quinazolinones, quinolines, quinoline derivatives, quinoline-7-carboxylic acids, quinoxalines, spiroketalamines, strobilurins, sulfamoyl triazoles, sulphamides, tetrazolyloximes, thiadiazines, thiadiazole carboxamides, thiazole carboxanides, thiocyanates, thiophene carboxamides, toluamides, triazines, triazobenthiazoles, triazoles, triazole-thiones, triazolo-pyrimidylamine, valinamide carbamates, ammonium methyl phosphonates, arsenic-containing compounds, benyimidazolylcarbamates, carbonitriles, carboxanilides, carboximidamides, carboxylic phenylamides, diphenyl pyridines, furanilides, hydrazine carboxamides, imidazoline acetates, isophthalates, isoxazolones, mercury salts, organomercury compounds, organophosphates, oxazolidinediones, pentylsulfonyl benzenes, phenyl benzamides, phosphonothionates, phosphorothioates, pyridyl carboxamides, pyridyl furfuryl ethers, pyridyl methyl ethers, SDHIs, thiadiazinanethiones, thiazolidines.

Particularly preferred fungicidal combinations include the following where "I" designates compounds of formula (I) or an individual compound selected from the table T1: I+(.+/−.)-cis-1-(4-chlorophenyl)-2-(1H-1,2,4-triazol-1-yl)-cycloheptanol (huanjunzuo), I+(2RS)-2-bromo-2-(bromomethyl) glutaronitrile (bromothalonil), I+(E)-N-methyl-2-[2-(2,5-dimethylphenoxymethyl) phenyl]-2-methoxy-iminoacetamide, (mandestrobin), I+1-(5-bromo-2-pyridyl)-2-(2,4-difluorophenyl)-1,1-difluoro-3-(1,2,4-triazol-1-yl)propan-2-ol, I+1-methylcyclopropene, I+2-methyl-[[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]propanoic acid methyl ester, I +2-(1-tert-butyl)-1-(2-chlorophenyl)-3-(1,2,4-triazol-1-yl)-propan-2-ol (TCDP), I+2,4-D, I+2,4-DB, I +2,6-dichloro-N-(4-trifluoromethylbenzyl)-benzamide, I+2,6-dimethyl-[1,4] dithiino[2,3-c:5,6-c']dipyrrole-1,3,5,7(2H,6H)-tetraone, I+2-[[(1R,5S )-5-[(4-fluorophenyl)methyl]-1-hydroxy-2,2-dimethyl -cyclopentyl]methyl]-4H-1,2,4-triazole-3-thione I+2-[[3-(2-chlorophenyl)-2-(2,4-difluorophenyl)oxiran-2-yl]methyl]-4H-1,2,4-triazole-3-thione I+ametoctradin (imidium), I+2-[2-[(7,8-difluoro-2-methyl-3-quinolyl) oxy]-6-fluoro-phenyl]propan-2-ol I+2-[2-fluoro-6-[(8-fluoro-2-methyl-3-quinolyl)oxy]phenyl]propan-2-ol I+cyflufenamid, I+2-benzyl-4-chlorophenol (Chlorophene), I+3-(difluoromethyl)-N-(7-fluoro-1,1,3,3-tetramethyl-indan-4-yl)-1-methyl-pyrazole-4-carboxamide I+diclocymet, I+3-(difluoromethyl)-N-methoxy-1-methyl-N-[1-methyl-2-(2,4,6-trichlorophenyl)ethyl]pyrazole-4-carboxamide, I+3'-chloro-2-methoxy-N-[(3RS) -tetrahydro-2-oxofuran-3-yl]acet-2', 6'-xylidide (clozylacon), I+3-iodo-2-propinyl n-butylcarbamate (IPBC), I+4,4,5-trifluoro-3,3-dimethyl-1-(3-quinolyl)isoquinoline I+4,4-difluoro-3,3-dimethyl-1-(3-quinolyl)isoquinoline I +5-fluoro-3,3,4,4-tetramethyl-1-(3-quinolyl)isoquinoline I+9-fluoro-2,2-dimethyl-5-(3-quinolyl)-3H-1,4-benzoxazepine I+tebufloquin, I+4-CPA, I+5-fluoro-2-(p-tolylmethoxy)pyrimidin-4-amine I+ferimzone, I+acibenzolar, I+acibenzolar-S-methyl, I+allyl alcohol, I+ametoctradin, I+amisulbrom, I+anilazine, I+aureofungin, I+azaconazole, I+azafenidin, I+azithiram, I+azoxystrobin, I+benalaxyl, I+benalaxyl-M, I +benalaxyl-M (kiralaxyl), I+benomyl, I+benthiavalicarb, I+benthiazole (TCMTB), I+benzalkonium chloride, I+benzamorf, I+benzovindiflupyr (solatenol), I+bethoxazin, I+biphenyl, I+bitertanol (biloxazol), I+bixafen, I+BLAD, I+blasticidin-S, I+Bordeaux mixture, I+boscalid, I+bromuconazole, I+bupirimate, I+but-3-ynyl N-[6-[[(Z)-[(1-methyltetrazol-5-yl)-phenyl-methylene]amino]oxymethyl]-2-pyridyl]carbamate I+dazomet, I+butylamine, I+calcium polysulfide, I+captafol, I+captan, I+carbaryl, I+carbendazim, I+carbendazim chlorhydrate, I+carboxin, I+CAS 517875-34-2 (DAS777), I+chinomethionate, I+chinomethionate (oxythioquinox, quinoxymethionate), I+chitosan, I+chlobenthiazone, I+chlorfenazole, I+chlormequat, I+chloroneb, I+chloropicrin, I+chlorothalonil, I+chlozolinate, I+climbazole, I+clofencet, I +copper acetate, I+copper carbonate, I+copper hydroxide, I+copper naphthenate, I+copper oleate, I+copper oxychloride, I+copper oxyquinolate, I+copper silicate, I+copper sulphate, I+copper tallate, I+coumoxystrobin, I+cresol, I+cuprous oxide, I+cyazofamid, I+cyclafuramid, I+cymoxanil, I+cyproconazole, I+cyprodinil, I+daracide, I+dichlofluanid, I+dichlorophen (dichlorophene), I+dichlorprop, I+diclomezine, I+dicloran, I+diethofencarb, I+difenoconazole, I+difenzoquat, I+diflumetorim, I+dimetachlone (dimethaclone), I+dimetconazole, I+dimethipin, I+dimethirimol, I+dimethomorph, I+dimoxystrobin, I+dingjunezuo (Jun Si Qi), I+diniconazole, I+diniconazole-M, I+, I+dinobuton, I+dinocap, I+dinocton, I+dinopenton, I+diphenylamine, I+dipyrithione, I+ditalimfos, I+dithianon, I+dithioether, I+dodemorph, I+dodicin, I+dodine, I+doguadine, I+drazoxolon, I+edifenphos, I+endothal, I+enestroburin, enoxastrobin I+fenamistrobin, I+epoxiconazole, I+etaconazole, I+etem, I+ethaboxam, I+ethephon, I+ethoxyquin, I+famoxadone, I+fenamidone, I+fenarimol, I+fenbuconazole, I +fenfuram, I+fenhexamid, I+fenoxanil, I+fenpiclonil, I+fenpropidin, I+fenpropimorph, I+fenpyrazamine, I+fentin acetate, I+fentin hydroxide, I+ferbam, I+fluazinam, I+fludioxonil, I+flufenoxystrobin, I+flumetralin, I+flumorph, I+fluopicolide, I+fluopicolide (flupicolide), I+fluopyram, I+fluoroimide, I+fluoxastrobin, I+fluquinconazole, I+flusilazole, I+flusulfamide, I+flutianil, I+flutolanil, I+flutriafol, I+fluxapyroxad, I+folpet, I+forchlorfenuron, I+fosetyl, I+fuberidazole, I+furalaxyl, I+furametpyr, I+gibberellic acid, I+gibberellins, I+guazatine, I+hexachlorobenzene, I+hexaconazole, I+hymexazol, I+hymexazole, hydroxyisoxazole I+imazalil, I+I+etridiazole, I+imazalil, I+imazalil sulphate, I+imibenconazole, I+iminoctadine, I+iminoctadine triacetate, I+iodocarb (isopropanyl butylcarbamate), I+ipconazole, I+iprobenfos, I+iprodione, I+iprovalicarb, I+isofetamid, I+isopropanyl butylcarbamate (iodocarb), I+isoprothiolane, I+isopyrazam, I+isotianil, I+kasugamycin, I+kresoxim-methyl, I+KSF-1002, I+maleic hydrazide, I+mancozeb, I+mandestrobin, I+mandipropamid, I+maneb, I+mepanipyrim, I+mepiquat, I+mepronil, I+meptyldinocap, I+metalaxyl, I+metalaxyl-M (mefenoxam), I +metam, I+metaminostrobin, I+metconazole, I+methyl bromide, I+methyl iodide, I+methyl isothiocyanate, I+metiram (polyram), I+metiram-zinc, I+metominostrobin, I+metrafenone, I+m-phenylphenol, I+myclobutanil, I+N'-(2,5-Dimethyl-4-phenoxy-phenyl)-N-ethyl-N-methyl-formamidine, I+N'-[4-(4,5-Dichloro-thiazol-2-yloxy)-2,5-dimethyl-phenyl]-N-ethyl-N-methyl-formamidine, I+N'-[4-[[3-[(4-chlorophenyl) methyl]-1,2,4-thiadiazol-5-yl]oxy]-2,5-dimethyl-phenyl]-N-ethyl-N-methyl-formamidine, I+ethirimol, I+N-(2-p-chlorobenzoylethyl)-hexaminium chloride, I+N-[(5-chloro-2-isopropyl-phenyl)methyl]-N-cyclopropyl-3-(difluoromethyl)-5-fluoro-1-methyl-pyrazole-4-carboxamide I+N-cyclopropyl-3-(difluoromethyl)-5-fluoro-N-[(2-isopropylphenyl)methyl]-1-methyl-pyrazole-4-carboxamide I+carpropamid, I+nabam, I+naphthalene acetamide, I+NNF-0721, I+octhilinone, I+ofurace, I+orysastrobin, I+osthol, I+oxadixyl, I+oxasulfuron, I+oxathiapiprolin, I+oxine-copper, I+oxolinic acid, I+oxpoconazole, I+oxycarboxin, I+paclobutrazol, I+pefurazoate, I+penconazole, I+pencycuron, I+penflufen, I+penthiopyrad, I+phenamacril, I+phosdiphen, I+phosetyl-Al, I+phosetyl-Al (fosetyl-al), I+phosphorus acids, I+phthalide (fthalide), I+picarbutrazox, I+picoxystrobin, I+piperalin, I+polycarbamate, I+polyoxin D (polyoxrim), I+p-phenylphenol, I+probenazole, I+prochloraz, I+procymidone, I+prohexadione, I+prohexadione-calcium, I+propamidine, I+propamocarb, I+propiconazole, I+propineb, I +propionic acid, I+proquinazid, I+prothioconazole, I+pyraclostrobin, I+pyrametostrobin, I+pyraoxystrobin, I+pyrazophos, I+pyribencarb (KIF-7767), I+pyrifenox, I+pyrimethanil, I+pyriofenone (IKF-309), I+pyroquilon, I+quinoxyfen, I+quintozene, I+sedaxane, I+silthiofam, I+simeconazole, I+spiroxamine, I+streptomycin, I+sulphur, I+tebuconazole, I+tebufloquin, I+tecloftalam, I+tecnazene, (TCNB), I+tetraconazole, I+thiabendazole, I+thicyofen, I+thidiazuron, I+thifluzamide, I+thiophanate-methyl, I+thiram, I+tiadinil, I+tioxymid, I+tolclofos-methyl, I+tolprocarb, I+tolylfluanid, I+triadimefon, I +triadimenol, I+triazoxide, I+tribromophenol (TBP), I+tribufos (tributyl phosphorotrithioate), I+triclopyricarb, I+tricyclazole, I+tridemorph, I+trifloxystrobin, I+triflumizole, I+triforine, I+trinexapac, I+triticonazole, I+uniconazole, I+validamycin, I+valifenalate, I+vapam, I+vapam (metam sodium), I+vinclozolin, I+zineb, I+ziram, I+zoxamide, I+α-naphthalene acetic acid.

Compounds of this invention can also be mixed with one or more further pesticides including insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection.

Examples of such agricultural protectants with which compounds of this invention can be formulated are:

Insecticides such as abamectin, acephate, acetamiprid, amidoflumet (S-1955), avermectin, azadirachtin, azinphosmethyl, bifenthrin, bifenazate, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron;

Bactericides such as streptomycin;

Acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and Biological agents such as *Bacillus thuringiensis, Bacillus thuringiensis* delta endotoxin, baculovirus, and entomopathogenic bacteria, virus and fungi.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds may also be applied to seeds to protect the seeds and seedlings developing from the seeds. The compounds may also be applied through irrigation water to treat plants.

The present invention envisages application of the compounds of the invention to plant propagation material prior to, during, or after planting, or any combination of these.

Although active ingredients can be applied to plant propagation material in any physiological state, a common approach is to use seeds in a sufficiently durable state to incurr no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate;

salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha. Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80 ° A
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| Suspension concentrate | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

PREPARATION EXAMPLES

The following examples illustrate the above-described invention in greater detail without limiting it.

Example 1

Synthesis of 5-chloro-6-(2-furyl)-1-hydroxy-3H-2,1-benzoxaborole (Compound No. 33)

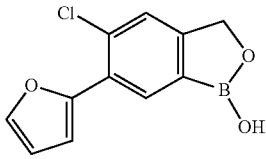 [SMILES: OB1OCc2cc(Cl)c(-c3ccco3)cc21]

Under argon, 5-chloro-1-hydroxy-3H-2,1-benzoxaborol-6-amine (5.67 g, 30.0 mmol, 97 mass %) was dissolved in furan (55.0 mL, 25.0 equiv., 99 mass %) and acetonitrile (105 mL, 3.5 mL/mmol, 99.9 mass %). Temperature of the mixture was increased to 35° C. (reflux) and hydrobromic acid (0.17 mL, 0.05 equiv., 48 mass % in water) was added followed by tert-butyl nitrite (6.00 mL, 1.50 equiv., 90 mass %) dropwise.
Important gas release was observed. It was stirred for 2 h at 35-45° C. The mixture was directly evaporated and the crude obtained subject to flash chromatography over silicagel with dichloromethane/methanol 99:1 to 97.5:2.5 as eluant. 5-chloro-6-(2-furyl)-1-hydroxy-3H-2,1-benzoxaborole (3.9 g, 16 mmol, 98 mass %, 54% Yield) was obtained as a solid (melting point: 142-147° C.).
$^1$H NMR (400 MHz, DMSO-$d_6$) δ ppm 5.02 (s, 2 H), 6.67 (dd, J=3.30, 1.83 Hz, 1 H), 7.10 (d, J=3.67 Hz, 1 H), 7.64 (s, 1 H), 7.85 (s, 1 H), 8.21 (s, 1 H), 9.47 (br. s., 1 H)
LC-MS: RT 0.93 Min 235/237 [M+H]+

Example 2

Synthesis of 5-(5-chloro-1-hydroxy-3H-2,1-benzoxaborol-6-yl)furan-2-carbaldehyde

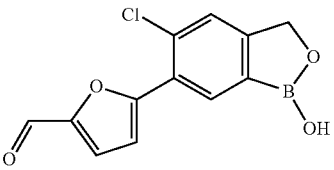

Under argon, a fine suspension of 5-chloro-1-hydroxy-3H-2,1-benzoxaborol-6-amine (1.89 g, 10.0 mmol, 97 mass %) and furfural (13.5 mL, 16 equiv., 98 mass %) was stirred in acetonitrile (20.0 mL, 2.0 mL/mmol, 99.9 mass %). Temperature of the mixture was increased to 45° C. and hydrobromic acid (0.060 mL, 0.05 equiv., 48 mass % in water) was added followed by tert-butyl nitrite (2.00 mL, 1.50 equiv., 90 mass %) dropwise. Important gas release was observed. It was stirred for 2h at 45° C. The mixture was directly evaporated and the crude obtained subject to flash chromatography over silicagel with dichloromethane/methanol 99:1 to 97:3 as eluant. 5-(5-chloro-1-hydroxy-3H-2,1-benzoxaborol-6-yl)furan-2-carbaldehyde (416 mg, 1.363 mmol, 86 mass %, 13.6% Yield) was obtained as a solid (melting point: 145-165° C.).
$^1$H NMR (400 MHz, Acetone) δ ppm 5.08 (s, 2 H), 7.35 (d, J=3.67 Hz, 1 H), 7.62 (d, J=3.67 Hz, 1 H), 7.67 (s, 1 H), 8.35 (s, 1 H), 8.52 (s, 1 H), 9.71 (s, 1 H)
LC-MS: RT 0.84 Min 263/265 [M+H]+

Example 3

Synthesis of 1-[5-(5-chloro-1-hydroxy-3H-2,1-benzoxaborol-6-yl)-2-furyl]-N-methoxy-methanimine

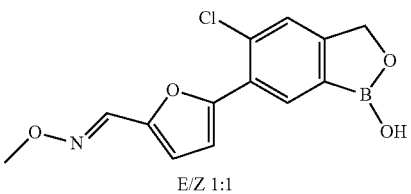 [SMILES: CO/N=C/c1ccc(-c2cc3c(cc2Cl)COB3O)o1]

E/Z 1:1

To a stirred solution of 5-(5-chloro-1-hydroxy-3H-2,1-benzoxaborol-6-yl)furan-2-carbaldehyde (0.263 g, 0.862 mmol, 86 mass %) in methanol (4.3 mL, 5.0 mL/mmol, 99.5 mass %) was added pyridine (0.12 mL, 1.7 equiv., 99.8 mass %) followed by methoxyamine hydrochloride (0.12 g, 1.6 equiv., 97 mass %). The mixture was stirred 18 h at 23° C. Methanol was removed under reduced pressure and the residue poured in 1 N hydrochloric acid which was extracted with DCM. Organics were combined, washed with brine, dried over sodium sulfate, filtered and evaporated under reduced pressure to afford 1-[5-(5-chloro-1-hydroxy-3H-2,1-benzoxaborol-6-yl)-2-furyl]-N-methoxy-methanimine (275 mg, 0.8491 mmol, 90 mass %, 98.5% Yield) as a gum.
LC-MS: 2 peaks RT 0.97 and 1.00 Min 292/294 [M+H]+

Example 4

Synthesis of 5-(5-chloro-1-hydroxy-3H-2,1-benzoxaborol-6-yl)furan-2-carbaldehyde oxime

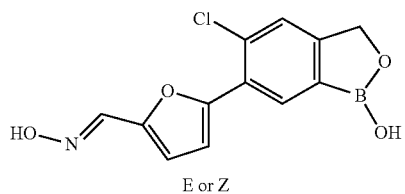 [SMILES: O/N=C/c1ccc(-c2cc3c(cc2Cl)COB3O)o1]

E or Z

To a stirred solution of 5-(5-chloro-1-hydroxy-3H-2,1-benzoxaborol-6-yl)furan-2-carbaldehyde (0.100 g, 0.328 mmol, 86 mass %) in methanol (1.6 mL, 5.0 mL/mmol, 99.5 mass %) was added pyridine (0.045 mL, 1.7 equiv., 99.8 mass %) followed by hydroxylamine hydrochloride (37 mg, 1.6 equiv., 99 mass %). The mixture was stirred 18h at 23° C. Water was added to the mixture which was acidified to pH 3 with hydrochloric acid. The mixture was stirred for 30 min and the fine yellow solid obtained was filtered and washed with water then heptane. The solid was finally dried in the vacuum oven. 5-(5-chloro-1-hydroxy-3H-2,1-benzoxaborol-6-yl)furan-2-carbaldehyde oxime (89 mg, 0.3047 mmol, 95 mass %, 93.0% Yield) was obtained as a yellow solid (melting point: 188-193° C.). Stereochemistry of the double bond was not defined.
$^1$H NMR (400 MHz, Aceton+D$_2$O) δ ppm 5.08 (s, 2 H), 7.26 (d, J=3.30 Hz, 1 H), 7.42 (d, J=3.67 Hz, 1 H), 7.57 (s, 1 H), 7.64 (s, 1 H), 8.31 (s, 1 H)
LC-MS: RT 0.84 Min 278/280 [M+H]+

Example 5:

Synthesis of (1-methyl-2-oxo-propyl) 5-fluoro-1-hydroxy-3H-2,1-benzoxaborole-6-carboxylate

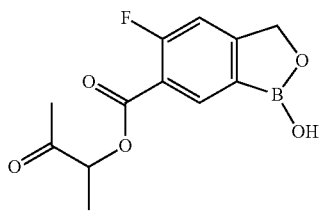 [SMILES: CC(=O)C(C)OC(=O)c1cc2c(cc1F)COB2O]

To a stirred solution of 5-fluoro-1-hydroxy-3H-2,1-benzoxaborole-6-carboxylic acid (0.25 g, 1.3 mmol) in tetrahydrofuran (10 mL/g), 3-hydroxybutan-2-one (0.133 g, 1.56 mmol), 1-Ethyl-3-(3-dimethylaminopropyl) carbodiimide hydrochloride (0.270 g, 1.4 mmol) and DMAP (0.031 g, 0.26 mmol) were added and the reaction mass was stirred at ambient temperature under nitrogen atmosphere for 5 hrs. Reaction mixture was diluted 10 ml water and then acidified with dil. HCl (till pH~3). The aqueous layer was extracted with dichloromethane (3×50 ml). The combined organic layer were washed with brine solution (10 ml) and then dried over sodium sulfate, filtered over celite pad and evaporated to afford the crude. The crude mass was subjected to flash chromatography over silicagel (4 g pre packed column) using dichloromethane/methanol 95:5 to 80:20 as eluent to yield (1-methyl-2-oxo-propyl) 5-fluoro-1-hydroxy-3H-2,1-benzoxaborole-6-carboxylate (50 mg, 0.1880 mmol, 15% Yield) as white solid.
$^1$H NMR (400 MHz, DMSO-d6) δ ppm 9.45 (s, 1H), 8.35 (d, J=7.5 Hz, 1H), 7.44 (d, J=11.3 Hz, 2H), 5.34 (q, J=7.0 Hz, 1H), 5.05 (s, 2H), 2.22 (s, 3H), 1.48 (d, J=7.0 Hz, 3H).
LC-MS: RT 0.63 Min 267.3 [M+H]+

Example 6

Synthesis of 2-(5-fluoro-1-hydroxy-3H-2,1-benzoxaborol-6-yl)-4,5-dimethyl-oxazole

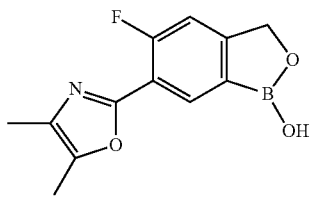 [SMILES: Cc1nc(-c2cc3c(cc2F)COB3O)oc1C]

To a solution of (1-methyl-2-oxo-propyl) 5-fluoro-1-hydroxy-3H-2,1-benzoxaborole-6-carboxylate (0.15 g, 0.56 mmol) in acetic acid (10 mL/g), 0.5 M ammonia (10 equiv., 5.6 mmol) was added and reaction mixture was heated in reflux at 100° C. for 12 hrs under nitrogen atmosphere.
Reaction mixture was cooled to ambient temperature and diluted with ethyl acetate. The organic layer was then washed with water, brine solution, dried over anhydrous sodium sulphate and concentrated to obtain crude mass. The crude mass was subjected to flash chromatography over silicagel (4 g pre packed column) using dichloromethane/methanol 95:5 to 90:10 as eluent to yield 2-(5-fluoro-1-hydroxy-3H-2,1-benzoxaborol-6-yl)-4,5-dimethyl-oxazole (0.060 g, 0.24 mmol, 43% Yield) as white solid.
$^1$H NMR (DMSO-d6, 400MHz): δ (ppm) 9.37 (s, 1H), 8.37 (d, J=7.6 Hz, 1H), 7.43 (d, J=11.2 Hz, 1H), 5.03 (s, 2H), 2.33 (s, 3H), 2.07-2.14 (m, 3H).
LC-MS: RT 1.54 Min 248 [M+H]+

Example 7

Synthesis of 5-fluoro-1-hydroxy-6-iodo-3H-2,1-benzoxaborole

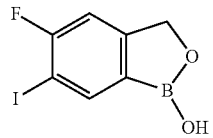 [SMILES: OB1OCc2cc(F)c(I)cc21]

To a solution of PTSA monohydrate (6.15 g, 3 equiv., 35.94 mmol, 100 mass %) in acetonitrile (25.0 mL, 99.5 mass %) was added 5-fluoro-1-hydroxy-3H-2,1-benzoxaborol-6-amine (2.0 g, 11.98 mmol, 100 mass %) and the grey suspension obtained was stirred for 10 min at 20° C. The mixture was cooled to 0° C. and a solution of sodium nitrite (1.66 g, 2.0 equiv., 23.96 mmol, 99 mass %) and potassium iodide (5.02 g, 2.5 equiv., 29.95 mmol, 99 mass %) in water (5 mL, 100 mass %) was added drop wise (1 h) via dropping funnel. During addition the mixture turned dark brown quickly, gas release was observed and mixture became thicker. The mixture was stirred at 20° C. for 1 h. The reaction mass was diluted with water (50 mL) and sat. sodium hydrogen carbonate (25 mL) and 2 M sodium thiosulfate (25 mL) were added. The crude was extracted with ethyl acetate (3×30 ml). Combined organics were washed with water, dried over sodium sulfate, evaporated under reduced pressure to afford the crude as red solid. The crude was subject to flash chromatography over silica gel (110 g pre packed column) with Cyclohexane/Ethyl acetate 99.5:0.5 to 20:80 as eluent to obtain 5-fluoro-1-hydroxy-6-iodo-3H-2,1-benzoxaborole (1.4 g, 5 mmol, 100 mass %, 42% Yield) was obtained as a white solid.
$^1$H NMR (400 MHz, DMSO-d$_6$) δ ppm 4.94 (s, 2 H), 7.36 (s, 1 H), 8.16 (s, 1 H), 9.32 (s, 1 H)
LCMS : RT 1.72 Min 276.8 [M-H]+

Example 8

Synthesis of N8-(5-fluoro-6-iodo-3H-2,1-benzoxaborol-1-yl)-N1,N1,N8-trimethyl-naphthalene-1,8-diamine

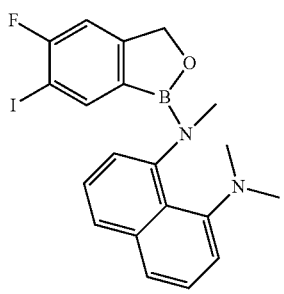 [SMILES: CN(C)c1cccc2cccc(N(C)B3OCc4cc(F)c(I)cc43)c12]

To a stirred solution of 5-fluoro-1-hydroxy-6-iodo-3H-2,1-benzoxaborole (1.38 g, 4.9 mmol, 95 mass %) in toluene (100 mL, 99.9 mass%) was added N1,N1,N8-trimethylnaphthalene-1,8-diamine (0.99 g, 4.9 mmol, 99.8 mass %) at 23° C. under argon. The reaction mass was stirred for 1 h at 120° C. accompanied by azeotropic removal of water. Toluene was distilled off to obtain the crude mass. The crude mass was washed with ethyl acetate and then vacuum dried to afford (N8-(5-fluoro-6-iodo-3H-2,1-benzoxaborol-1-yl)-N 1,N1,N8-trimethyl-naphthalene-1,8-diamine (1.6 g, 3.5 mmol, 95 mass %, 70% Yield) as a pale yellow solid.

$^1$H NMR (400 MHz, DMSO-d6) δ ppm 2.68 - 2.75 (m, 6 H) 2.80 (s, 3 H) 5.01 (s, 2 H) 6.18 (br. s., 1 H) 6.53 (d, J=7.78 Hz, 1 H) 7.07 (d, J=8.78 Hz, 1 H) 7.16 (d, J=7.53 Hz, 1 H) 7.40-7.56 (m, 3 H) 7.85 (dd, J=7.78, 1.25 Hz, 1 H)

LCMS : RT 2.19-2.32 Min 460.9 [M+H]+

Example 9

Synthesis of N8-[6-(6-chloro-3-pyridyl)-5-fluoro-3H-2,1-benzoxaborol-1-yl]-N1,N1,N8-trimethyl-naphthalene-1,8-diamine

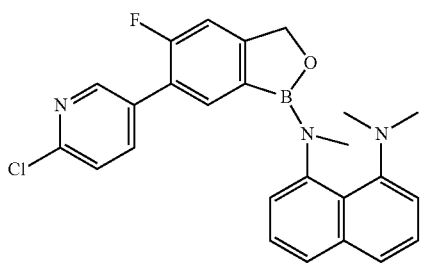 [SMILES: CN(C)c1cccc2cccc(N(C)B3OCc4cc(F)c(-c5ccc(Cl)nc5)cc43)c12]

To a solution of N8-(5-fluoro-6-iodo-3H-2,1-benzoxaborol-1-yl)-N1,N1,N8-trimethyl-naphthalene-1,8-diamine (0.25 g, 0.54 mmol, 95 mass %) in tetrahydrofuran (5 mL, 99.5 mass %), was added (6-chloro-3-pyridyl) boronic acid (0.11 g, 0.71 mmol, 98 mass %), Cesium fluoride (0.17 g, 1.1 mmol, 99.0 mass %) and Bis(tri-t-butylphosphine)palladium(0) (0.138 g., 0.027 mmol, 98 mass %) under nitrogen. The solution was stirred at 60° C. for 18 h. The solvent was removed under reduced pressure and the residue thus obtained was dissolved in ethyl acetate. The organic phase was washed with water, dil. HCl (pH 3), water and brine. It was then dried over sodium sulfate, filtered over celite pad and evaporated to afford the crude which was subject to flash chromatography over silica gel (4 g pre packed column) with cyclohexane/ethyl acetate 95:5 to 8:2 as eluent. After evaporation of fractions the solid obtained was. N8-[6-(6-chloro-3-pyridyl)-5-fluoro-3H-2,1-benzoxaborol-1 1-yl]-N1,N1,N8-trimethyl-naphthalene-1,8-diamine (0.09 g, 0.2 mmol, 95 mass %, 40% Yield) was obtained as a pale yellow solid.

$^1$H NMR (400 MHz, DMSO-d6) δ ppm 2.77 (s,6H) 2.83 (s, 3H) 5.07 (s, 2 H) 5.88-6.08 (m, 1 H) 6.53 (d, J=7.78 Hz, 1 H) 7.12 (d, J=8.10 Hz, 1 H) 7.16 (d, J=10.93 Hz, 1 H) 7.28 (s, J=6.20, 6.20 Hz, 1 H) 7.47-7.61 (m, 4 H) 7.82 (d, J=7.62 Hz, 1 H) 7.98 (br. s., 1 H)

Example 10

Synthesis of 2-chloro-5-(5-fluoro-1-hydroxy-3H-2,1-benzoxaborol-6-yl)pyridine

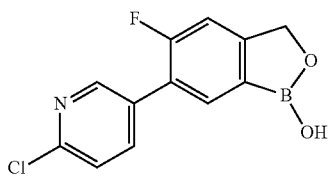 [SMILES: OB1OCc2cc(F)c(-c3ccc(Cl)nc3)cc21]

To a stirred solution of N8-[6-(6-chloro-3-pyridyl)-5-fluoro-3H-2,1-benzoxaborol-1-yl]-N1,N1,N8-trimethyl-naphthalene-1,8-diamine (0.09 g, 0.2 mmol, 95 mass %) in tetrahydrofuran I (2 mL, 99.5 mass %), Conc. HCl (4 mL 36 mass %) and 2 drop TFA was added. The mixture was stirred at ambient temperature for 18 hrs. The mixture was extracted with ethyl acetate and the organic phase was washed with water and brine. It was then dried over sodium sulfate, filtered over celite pad and evaporated to afford the crude which was subject to flash chromatography over silicagel (4 g prepacked column) with cyclohexane/ethyl acetate 95:5 to 8:2 as eluent. After evaporation of fractions the solid 2-chloro-5-(5-fluoro-1-hydroxy-3H-2,1-benzoxaborol-6-yl) pyridine (0.033 g, 0.13 mmol, 97 mass %, 60% Yield) was obtained as a white solid.

$^1$H NMR (400 MHz, DMSO-d$_6$) δ ppm 5.05 (s, 2 H) 7.39-7.49 (m, 1 H) 7.64-7.70 (m, 1 H) 7.84-7.91 (m, 1 H) 8.03-8.09 (m, 1 H) 8.52-8.63 (m, 1 H) 9.15-9.61 (m, 1 H)

LCMS: RT 1.71 Min 263.9 [M+H]$^+$

Example 11

Synthesis of N8-[5-fluoro-6-(3-thienyl)-3H-2,1-benzoxaborol-1-yl]-N1,N1,N8-trimethyl-naphthalene-1,8-diamine

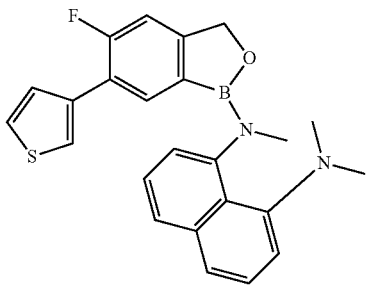 [SMILES: CN(C)c1cccc2cccc(N(C)B3OCc4cc(F)c(-c5ccsc5)cc43)c12]

To a solution of N8-(5-fluoro-6-iodo-3H-2,1-benzoxaborol-1-yl)-N1,N1,N8-trimethyl-naphthalene-1,8-diamine (0.25 g, 0.54 mmol, 95 mass %) in tetrahydrofuran (5 mL, 99.5 mass %), was added 3-thienylboronic acid (0.083 g., 0.65 mmol, 98 mass %), Cesium fluoride (0.17 g., 1.1 mmol, 99.0 mass %) and Bis(tri-t-butylphosphine) palladium(0) (0.014 g., 0.027 mmol, 98 mass %) under nitrogen. The solution was stirred at 60° C. for 18 h. Most of the solvent was removed under reduced pressure. The residue was dissolved in ethyl acetate and the organic phase was washed with water, and brine. It was then dried over sodium sulfate, filtered over celite pad and evaporated to afford the crude which was subject to flash chromatography over silicagel (4 g prepacked column) with cyclohexane/ethyl acetate 95:5 to 8:2 as eluent. After evaporation of fractions the solid obtained was N8-[5-fluoro-6-(3-thienyl)-3H-2,1-benzoxaborol-1-yl]-N1,N1,N8-trimethyl-naphthalene-1,8-diamine (0.1 g, 0.2 mmol, 95 mass %, 40% Yield) was obtained as a pale yellow solid.

$^1$H NMR (400 MHz, DMSO-d$_6$) δ ppm 2.64-2.78 (m, 6 H) 2.83 (s, 3 H) 5.04 (s, 2 H) 6.00-6.23 (m, 1 H) 6.53 (d, J=7.78 Hz, 1 H) 6.68-6.77 (m, 1 H) 7.01-7.09 (m, 1 H) 7.12-7.19 (m, 1 H) 7.22-7.28 (m, 1 H) 7.37-7.44 (m, 1 H) 7.45-7.58 (m, 3 H) 7.76-7.90 (m, 1 H)

LCMS: RT 2.19 Min 416.9 [M+H]$^+$

Example 12

Synthesis of 5-fluoro-1-hydroxy-6-(3-thienyl)-3H-2,1-benzoxaborole

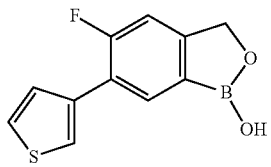 [SMILES: OB1OCc2cc(F)c(-c3ccsc3)cc21]

To a stirred solution of N8-[5-fluoro-6-(3-thienyl)-3H-2,1-benzoxaborol-1-yl]-N1, N1,N8-trimethyl-naphthalene-1,8-diamine (0.075 g, 0.18 mmol, 95 mass %) in tetrahydrofuran (2 mL, 99.5 mass %) Conc. HCl (4 mL 36 mass %) and 2 drop TFA was added. The mixture was stirred at ambient temperature for 18 hrs. The mixture was extracted with ethyl acetate and the organic phase was washed with water, water (pH 3), water and brine. It was then dried over sodium sulfate, filtered over celite pad and evaporated to afford the crude which was subject to flash chromatography over silicagel (4 g pre packed column) with cyclohexane/ethyl acetate 95:5 to 80:20 as eluent to afford 5-fluoro-1-hydroxy-6-(3-thienyl)-3H-2,1-benzoxaborole (0.032 g, 0.13 mmol, 97 mass %, 70% Yield) was obtained as a Off white gummy solid.

$^1$H NMR (400 MHz, DMSO-d6) δ ppm 5.01 (s, 2 H) 7.37 (d, J=11.54 Hz, 1 H) 7.46 (dt, J=5.02, 1.51 Hz, 1 H) 7.69 (dd, J=5.02, 3.01 Hz, 1 H) 7.77-7.86 (m, 1 H) 8.00 (d, J=8.03 Hz, 1 H) 9.28 (br. s., 1 H)

LCMS: RT 1.79 Min 235 [M+H]$^+$

Example 13

Synthesis of 3-bromo-4-(bromomethyl) benzonitrile

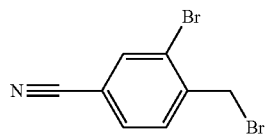 [SMILES: N#Cc1ccc(CBr)c(Br)c1]

To a stirred solution of 3-bromo-4-methyl-benzonitrile (2 g, 10.2014 mmol, 100 mass %) in carbon tetrachloride (20 mL, 100 mass %) under argon, was added NBS (2.2 g., 12.2417 mmol, 99 mass %) and benzoyl peroxide (0.123 g., 0.5101 mmol, 100 mass %). The mixture was heated to 85° C. for 18 h. The reaction mass was diluted with water (50 ml) and extracted with ethyl acetate. Organics were washed again with water and brine, dried and evaporated to afford 3-bromo-4-(bromomethyl) benzonitrile (1.2 g, 4.4 mmol, 90 mass %, 95% Yield) as an off white solid solid.

$^1$H NMR (400 MHz, chloroform-d) δ ppm 3.89-4.01 (m, 2 H) 6.61-6.77 (m, 1 H) 6.92-7.07 (m, 2 H)

LCMS: RT 1.12-1.49 Min 274 [M+H]$^+$

Example 14

Synthesis of (2-bromo-4-cyano-phenyl)methyl acetate

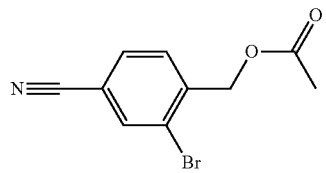

To a stirred solution of 3-bromo-4-(bromomethyl)benzonitrile (0.4 g, 1 mmol, 100 mass % in DMF (5 mL, 100 mass %) under argon, was added potassium acetate (0.4 g., 4 mmol, 97 mass %) The mixture was heated to 70° C. for 3hr. The reaction mass was diluted with water (50 ml) and extracted with ethyl acetate. Organics were washed again with water and brine, dried and evaporated to afford (2-bromo-4-cyano-phenyl)methyl acetate (0.3 g, 1 mmol, 90 mass %, 80% Yield) as a off white solid.

$^1$H NMR (400 MHz, chloroform-d) δ ppm 2.20 (s, 3 H) 5.23 (s, 2 H) 7.51-7.57 (m, 1 H) 7.61-7.67 (m, 1 H) 7.86-7.91 (m, 1 H)

Example 15

Synthesis [2-bromo-4-(1H-tetrazol-5-yl)phenyl] methyl acetate

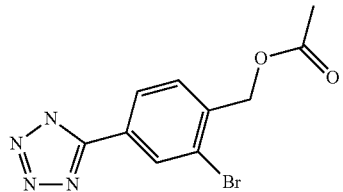 [SMILES: CC(=O)OCc1ccc(-c2nnn[nH]2)cc1Br]

To a stirred solution of (2-bromo-4-cyano-phenyl)methyl acetate (3.2 g, 13 mmol, 100 mass %) in DMF (20 mL, 99.8 mass %) under argon, was added sodium azide (1.2 g., 18 mmol, 99 mass %) and indium (III) chloride (0.56 g., 2.5 mmol). The mixture was heated for 2 hr at 140° C. in a sealed tube. The mixture was cooled to 0° C. and neutralized with 1N HCl. Aqueous layer was extracted with ethyl acetate (3×50 ml) .Organics were washed again with water and brine, dried and evaporated to afford [2-bromo-4-(1H-tetrazol-5-yl)phenyl]methyl acetate (2.6 g, 8.8 mmol, 90 mass %, 69% Yield) as a Off white solid $^1$H NMR (400 MHz, chloroform-d) δ ppm 2.17-2.29 (m, 3 H) 5.27 (s, 2 H) 7.50-7.62 (m, 1 H) 8.08-8.17 (m, 1 H) 8.36-8.43 (m, 1 H)

Example 16

Synthesis [[2-bromo-4-(2-methyltetrazol-5-yl)phenyl]methyl acetate

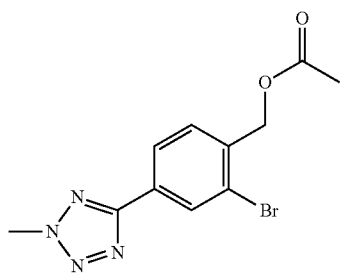 [SMILES: CC(=O)OCc1ccc(-c2nnn(C)n2)cc1Br]

To a stirred solution of [2-bromo-4-(1H-tetrazol-5-yl)phenyl]methyl acetate; (0.3 g, 0.9 mmol, 100 massc/o) in DMF (5 mL, 99.5 mass %) under argon, was added potassium carbonate (0.2 g., 1 mmol, 100 mass %) and iodomethane (0.1 g., 1 mmol, 100 mass %) at ambient temperature. Reaction mass was then stirred at ambient temperature for 1 hr. Reaction mixture was diluted with water (3×50 ml). The aqueous layer was extracted with ethyl acetate (3×50 ml) and the combined organic phase were washed with water, water (pH 3), water and brine. It was then dried over sodium sulfate, filtered over celite pad and evaporated to afford the crude which was subject to flash chromatography over silica gel (4 g prepacked column) with cyclohexane/ethyl acetate 95:5 to 8:2 as eluent., to afford [2-bromo-4-(2-methyltetrazol-5-yl)phenyl]methyl acetate (0.5 g, 0.46 mmol, 90 mass %, 50% Yield) as a white solid
$^1$H NMR (400 MHz, chloroform-d) δ ppm 2.20 (s, 3 H) 4.43 (s, 3 H) 5.26 (s, 2 H) 7.44-7.61 (m, 1 H) 7.88-8.16 (m, 1 H) 8.26-8.48 (m, 1 H)
LCMS: RT 1.29 Min 311 [M+H]$^+$

Example 17

Synthesis of [4-(2-methyltetrazol-5-yl)-2-(4,4,5,5-tetramethyl-1,3,2-dioxaborolan-2-yl) phenyl]methyl acetate

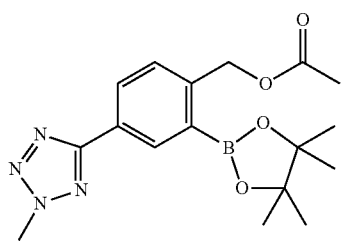 [SMILES: CC(=O)OCc1ccc(-c2nnn(C)n2)cc1B1OC(C)(C)C(C)(C)O1]

To a solution of [2-bromo-4-(2-methyltetrazol-5-yl)phenyl] methyl acetate (0.1 g, 0.3 mmol, 90 mass %) in toluene (10 mL/g, 100 mass %) was added bis(pinacolato)diborane (Pin$_2$B$_2$) (0.1 g, 0.5 mmol, 95.0 mass %), potassium acetate (0.09 g., 1 mmol, 99.999 mass %) and [1,1'-Bis (diphenylphosphino)ferrocene]dichloropalladium(II) complex with dichloromethane (1:1 ) (0.01 g., 0.02 mmol, 100 mass %) under nitrogen. The solution was stirred at 100° C. for 18 h. Most of the solvent was removed under reduced pressure. The residue was dissolved in ethyl acetate and the organic phase was washed with water, water (pH 3), water and brine. It was then dried over sodium sulfate, filtered over celite pad and evaporated to afford the crude which was subject to flash chromatography over silicagel (4 g prepacked column) with cyclohexane/ethyl acetate 95:5 to 8:2 as eluent. After evaporation of fractions the solid obtained was recrystallized in cyclohexane and [4-(2-methyltetrazol-5-yl)-2-(4,4,5,5-tetramethyl-1,3,2-dioxaborolan-2-yl)phenyl]methyl acetate (0.07 g, 0.2 mmol, 90 mass %, 60% Yield) was obtained as a gummy solid.
$^1$H NMR (400 MHz, chloroform-d) δ ppm 1.29 (s, 12 H) 2.02-2.07 (m, 3 H) 4.24-4.39 (m, 3 H) 5.27-5.42 (m, 2 H) 7.41-7.47 (m, 1 H) 8.10-8.19 (m, 1 H) 8.33-8.69 (m, 1 H)

Example 18

Synthesis of 5-(1-hydroxy-3H-2,1-benzoxaborol-6-yl)-2-methyl-tetrazole

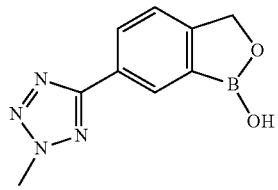 [SMILES: Cn1nnc(-c2ccc3c(c2)B(O)OC3)n1]

To a stirred solution of 4[4-(2-methyltetrazol-5-yl)-2-(4,4,5,5-tetramethyl-1,3,2-dioxaborolan-2-yl) phenyl]methyl acetate (0.3 g, 0.8 mmol, 98 mass %) in methanol (4 mL, 100 mass %) was added hydrochloric acid (4 mL, 110 mmol, 6 N). The mixture was stirred at RT for 18 hr Most of the solvent was removed under reduced pressure. The residue was dissolved in ethyl acetate and the organic phase was washed with water and brine. It was then dried over sodium sulfate, filtered over celite pad and evaporated to afford 5-(1-hydroxy-3H-2,1-benzoxaborol-6-yl)-2-methyl-tetrazole (0.15 g, 0.69 mmol, 100 mass %, 80% Yield).
1H NMR (400 MHz, DMSO-d6) δ ppm 4.44 (s, 3 H) 5.08 (s, 2 H) 7.60 (d, J=7.95 Hz, 1 H) 8.16 (dd, J=7.95, 1.47 Hz, 1 H) 8.50 (s, 1 H) 9.37 (s, 1 H)
LCMS: RT 0.32 Min 217 [M+H]$^+$

Example 19

Synthesis of 5-chloro-1-hydroxy-3H-2,1-benzoxaborole-6-carboxamide

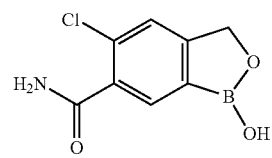 [SMILES: NC(=O)c1cc2c(cc1Cl)COB2O]

To a mixture of methyl 5-chloro-1-hydroxy-3H-2,1-benzoxaborole-6-carboxylate (5 g, 22.0826 mmol, 100 mass %) and aq ammonia (50 mL, 10 mL/g, 578 mmol, 25 mass %) was added lanthanum(III) trifluoromethanesulphonate (1.8 g, 0.1 equiv., 2.2083 mmol). The mixture was heated at 70° C. for 5 hours in a Parr pressure reactor. Reaction mixture was then concentrated and 20% methanol in dichloromethane was added, filtered over celite and concentrated to get crude compound LCMS was checked. The crude product was then purified by Combi flash using 0-20% MeOH in dichloromethane to obtain the pure product as white solid (2.5 g, 54%Yield).
$^1$H NMR (400 MHz, DMSO-d6) δ 9.38 (1H, s), 7.88 (1H, br. s.), 7.76 (1H, s), 7.56 (2H, s), 5.03 (2H, s,)

Example 20

Synthesis of 5-chloro-N-(dimethylaminomethylene)-1-hydroxy-3H-2,1-benzoxaborole-6-carboxamide

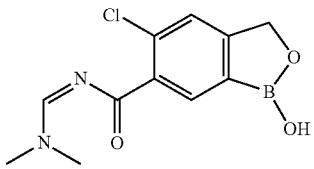 [SMILES: CN(C)/C=N\C(=O)c1cc2c(cc1Cl)COB2O]

To a solution of 5-chloro-1-hydroxy-3H-2,1-benzoxaborole-6-carboxamide (1 g, 4.7301 mmol, 100 mass %) in toluene (10 ml, 10 mL/g, 100 mass %) was added N,N- dimethylformamide dimethylacetal (1.16 mL, 2 equiv., 9.4603 mmol, 100 mass %). The reaction mixture was then heated at 100° C. for 2 h. Reaction mass was cooled to ambient temperature and the solvent was removed under vacuum to yield an oily residue as the crude product (1.5 gm), which was taken for the next step without any further purifications. Stereochemistry of the double bond was not defined.
LCMS: RT 0.5-0.75 Min 267/269.4 [M+H]$^+$ Example 21

Synthesis of 5-chloro-1-hydroxy-N-[(hydroxyamino)methylene]-3H-2,1-benzoxaborole-6-carboxamide

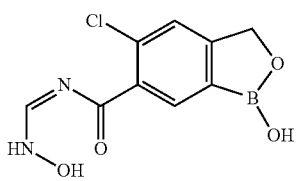 [SMILES: O=C(/N=C\NO)c1cc2c(cc1Cl)COB2O]

To a solution of hydroxylamine hydrochloride (0.47 g, 1.5 equiv., 6.8 mmol, 100 mass %) in acetic acid (12 ml, 10 mL/g, 100 mass %) was added 1 M sodium hydroxide solution (6.8 mL, 1.5 equiv., 6.8 mmol, 1 mol/L) drop wise and stirred for 15 minutes. 5-chloro-N-(dimethylaminomethylene)-1-hydroxy-3H-2,1-benzoxaborole-6-carboxamide (example 21, 1.2 g, 4.5 mmol, 100 mass %) was then added to the mixture and the resulting solution was stirred at ambient temperature for one hour. The solid precipitated out was filtered and vacuum dried to yield the pure product (0.43 g, 1.71 mmol, 38%Yield). Stereochemistry of the double bond was not defined.
$^1$H NMR (400 MHz, DMSO-d$_6$) δ ppm 5.03 (s, 2 H) 7.54-7.69 (m, 2H) 7.83 (s, 1 H) 9.42 (s, 1 H) 10.67-10.83 (m, 2 H)

LCMS: RT 0.27 Min 255 [M+H]$^+$

Example 22

Synthesis of 5-(5-chloro-1-hydroxy-3H-2,1-benzoxaborol-6-yl)-1,2,4-oxadiazole

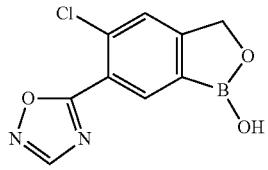 [SMILES: OB1OCc2cc(Cl)c(-c3ncno3)cc21]

A solution of 5-chloro-1-hydroxy-N-[(hydroxyamino)methylene]-3H-2,1-benzoxaborole-6-carboxamide (0.400 g, 1.57 mmol, 100 mass %) in acetic acid (4 mL, 69.7 mmol, 99.8 mass %) and 1,4-Dioxane (4 mL, 46.9 mmol, 99.9 mass %) was stirred at 90° C. for 1 h. The reaction mass was cooled to ambient temperature. The reaction mixture was evaporated to give crude residue. The residue was dissolved in ethyl acetate and the organic phase was washed with water and brine. It was then dried over sodium sulfate, filtered over celite pad and evaporated to afford the crude mass. The crude mass was subject to flash chromatography over silicagel (12 g prepacked column) with cyclohexane/ethyl acetate 70:30 as eluent to give pure product 5-(5-chloro-1-hydroxy-3H-2,1-benzoxaborol-6-yl)-1,2,4-oxadiazole (120 mg, 0.5076 mmol, 100 mass %, 32.3% Yield).
$^1$H NMR (400 MHz, DMSO-d$_6$) δ ppm 5.10 (s, 2 H) 7.85 (s, 1 H) 8.47 (s, 1 H) 9.22 (s, 1 H) 9.58 (s, 1 H)
LCMS: RT 1.55 Min 236.8[M+H]$^+$ Example 23

Synthesis of 5-(5-fluoro-1-hydroxy-3H-2,1-benzoxaborol-6-yl)-3-methyl-1,2,4-oxadiazole

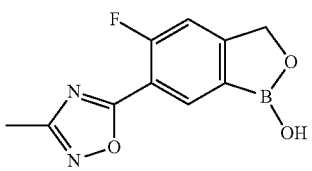 [SMILES: Cc1noc(-c2cc3c(cc2F)COB3O)n1]

To a solution of N'-hydroxyacetamidine (0.36 g, 4.7626 mmol, 100 mass %) in THF(10 ml) under nitrogen was added molecular sieves (1 gm) and sodium hydride (0.209 g, 5.2389 mmol, 60 mass %). The resulting suspension was heated for one hour at 60° C. A solution of methyl 5-fluoro-1-hydroxy-3H-2,1-benzoxaborole-6-carboxylate (500 mg, 2.3813 mmol, 100 mass %) in THF (10 ml) was added in drops to the reaction mass and was stirred for 18 h at 60° C. The reaction mixture was cooled to ambient temperature and quenched in 1NHCl solution and extracted with ethyl acetate. The organic phase was washed with water and brine. It was then dried over sodium sulfate, filtered over celite pad and evaporated to afford the crude mass. The crude mass was subject to flash chromatography over silicagel (12 g prepacked column) with cyclohexane/ethyl acetate 50:50 as eluent to give pure product -(5-fluoro-1-hydroxy-3H-2,1- benzoxaborol-6-yl)-3-methyl-1,2,4-oxadiazole (200 mg, 0.8547 mmol, 100 mass %, 35.89% Yield) as white solid
$^1$H NMR (400 MHz, DMSO-d$_6$) δ 2.45 (s, 3 H), 5.09 (s, 2 H), 7.59 (d, J=11.13 Hz, 1 H), 8.53 (d, J=7.34 Hz, 1 H), 9.50 (s, 1 H)
LCMS: RT 0.4 Min 235 [M+H]$^+$
TABLE T1
| Cmpd No. | Structures | RT (min) | [M − H]$^-$ | [M + H]$^+$ | Method | MP ° C. |
|---|---|---|---|---|---|---|
| | Characterising data: | | | | | |
| 1 | 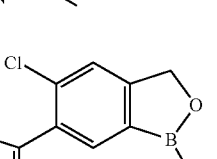 | 0.89 | | | | 155-160 |
| 2 | 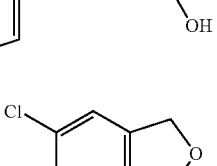 | | | | M1 | 142-147 |
| 3 | 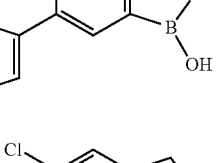 | | | | M1 | 125-135 |
| 4 | 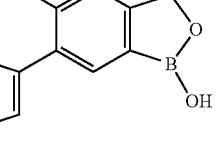 | | | | M1 | 195-202 |
| 5 | 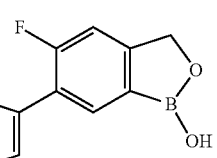 | | | | M1 | 155-164 |
| 6 | 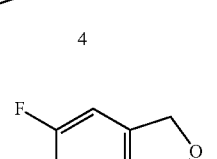 | | | | M1 | 134-140 |
| 7 | 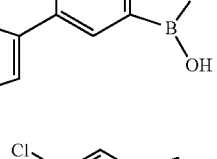 | 0.58 | | 246/248 | M1 | |

TABLE T1-continued
Characterising data:
| Cmpd No. | Structures | RT (min) | [M − H]⁻ | [M + H]⁺ | Method | MP ° C. |
|---|---|---|---|---|---|---|
| 8 | 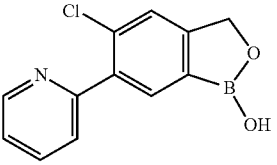 [SMILES: OB1OCc2cc(Cl)c(-c3ccccn3)cc21] | 0.7 | | 246/248 | M1 | |
| 9 | 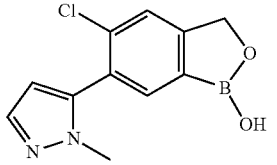 [SMILES: Cn1nccc1-c1cc2c(cc1Cl)COB2O] | 0.78 | | 249/251 | M1 | |
| 10 | 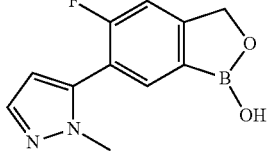 | 0.71 | | 233 | M1 | |
| 11 | 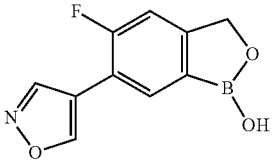 | 1.53 | | 219.9 | M2 | 230-232 |
| 12 | 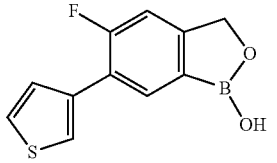 [SMILES: OB1OCc2cc(F)c(-c3ccsc3)cc21] | 1.76 | | 234.9 | M2 | |
| 13 | 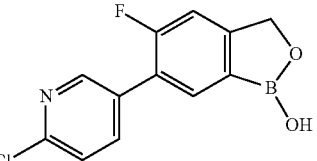 | 1.67 | | 263.9 | M2 | 213-215 |
| 14 | 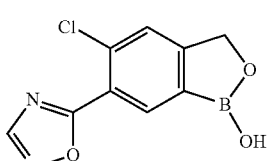 | 1.55 | | 236.8 | M2 | 175-177 |
| 15 | 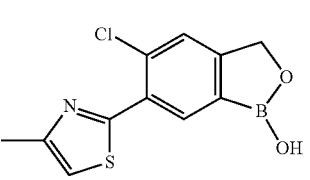 [SMILES: Cc1csc(-c2cc3c(cc2Cl)COB3O)n1] | 0.9 | | 266/268 | M1 | |

TABLE T1-continued

Characterising data:

| Cmpd No. | Structures | RT (min) | [M − H]⁻ | [M + H]⁺ | Method | MP ° C. |
|---|---|---|---|---|---|---|
| 16 | 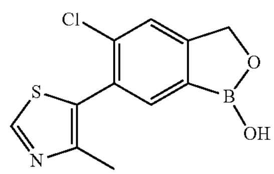 [SMILES: Cc1ncsc1-c1cc2c(cc1Cl)COB2O] | 0.82 | | 266/268 | M1 | |
| 17 | 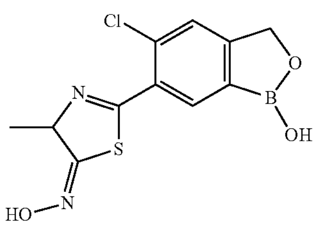 [SMILES: CC1N=C(c2cc3c(cc2Cl)COB3O)S/C1=N/O] | 0.79 | | 297/299 | M1 | |
| 18 | 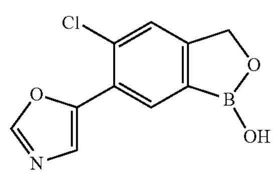 [SMILES: OB1OCc2cc(Cl)c(-c3cnco3)cc21] | 0.75 | | 236/238 | M1 | |
| 19 | 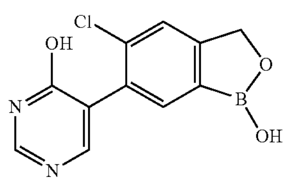 [SMILES: OB1OCc2cc(Cl)c(-c3cncnc3O)cc21] | 0.54 | | 263/265 | M1 | |
| 20 | 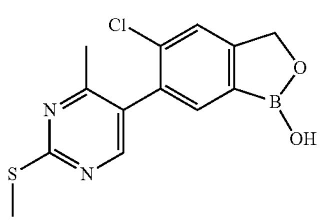 [SMILES: CSc1ncc(-c2cc3c(cc2Cl)COB3O)c(C)n1] | 0.95 | | 307/309 | M1 | |
| 21 | 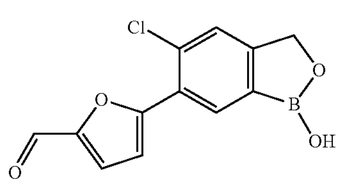 [SMILES: O=Cc1ccc(-c2cc3c(cc2Cl)COB3O)o1] | 0.84 | | 263/265 | M1 | 145-165 |
| 22 | 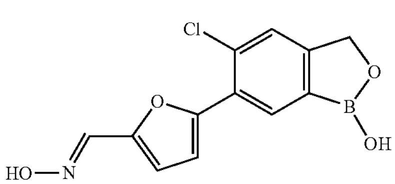 [SMILES: O/N=C/c1ccc(-c2cc3c(cc2F)COB3O)o1] | 0.84 | | 278/280 | M2 | 188-193 |

TABLE T1-continued

Characterising data:

| Cmpd No. | Structures | RT (min) | [M − H]⁻ | [M + H]⁺ | Method | MP ° C. |
|---|---|---|---|---|---|---|
| 23 | Chloro-benzoxaborole with furan-methoxime substituent | 0.97 and 1.00 | | 292/294 | M2 | |
| 24 | Chloro-benzoxaborole with phenylamino-methyl-cyclopropyl-pyrimidine | 1.13 | | 392/394 | M1 | |
| 25 | Chloro-benzoxaborole with thiazole | 0.83 | | 252/254 | M1 | |
| 26 | Fluoro-benzoxaborole with furan-aldehyde | 0.77 | | 246.9 | M1 | |
| 27 | Fluoro-benzoxaborole with furan-hydroxime | | | | M2 | 200-220 |
| 28 | Fluoro-benzoxaborole with furan-methoxime | | | | M2 | 125-140 |
| 29 | Fluoro-benzoxaborole with oxadiazole | 0.36 | | 221.2 | M3 | 204-206 |

TABLE T1-continued

| Cmpd No. | Structures | RT (min) | [M − H]⁻ | [M + H]⁺ | Method | MP ° C. |
|---|---|---|---|---|---|---|
| 30 | 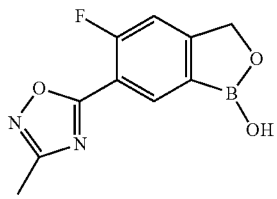 [SMILES: Cc1noc(-c2cc3c(cc2F)COB3O)n1] | 0.4 | | 235.24 | M3 | 200-202 |
| 31 | 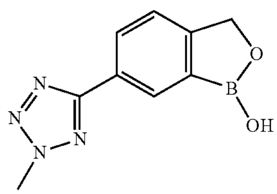 [SMILES: Cn1nnc(-c2ccc3c(c2)B(O)OC3)n1] | 0.32 | | 217.26 | M3 | 209-210 |
| 32 | 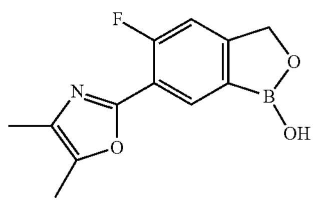 [SMILES: Cc1nc(-c2cc3c(cc2F)COB3O)oc1C] | 0.81 | | 248.18 | M3 | 164-166 |
| 33 | 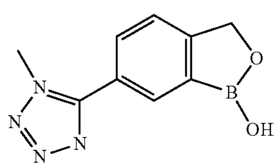 | 0.27 | | 217.16 | M3 | 181-183 |
| 34 | 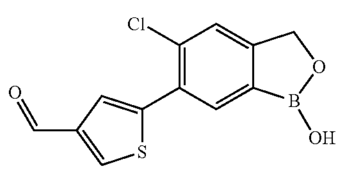 [SMILES: O=Cc1csc(-c2cc3c(cc2Cl)COB3O)c1] | 1.27 | 277 | | M1 | |
| 35 | 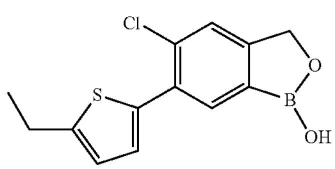 [SMILES: CCc1ccc(-c2cc3c(cc2Cl)COB3O)s1] | 1.71 | 277 | | M1 | |
| 36 | 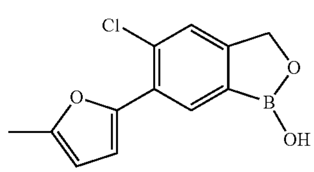 [SMILES: Cc1ccc(-c2cc3c(cc2Cl)COB3O)o1] | 1.52 | 247.1 | | M1 | |
| 37 | 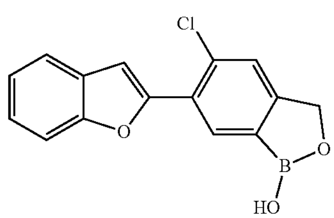 [SMILES: OB1OCc2cc(Cl)c(-c3cc4ccccc4o3)cc21] | 1.68 | 283.1 | | M1 | |

TABLE T1-continued

Characterising data:

| Cmpd No. | Structures | RT (min) | [M − H]⁻ | [M + H]⁺ | Method | MP ° C. |
|---|---|---|---|---|---|---|
| 38 | 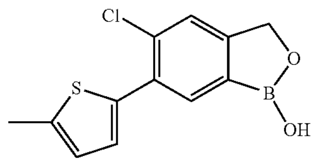 [SMILES: Cc1ccc(-c2cc3c(cc2Cl)COB3O)s1] | 1.59 | 263.1 | | M1 | |
| 39 | 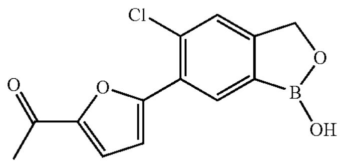 [SMILES: CC(=O)c1ccc(-c2cc3c(cc2Cl)COB3O)o1] | 1.26 | 275.1 | | M1 | |
| 40 | 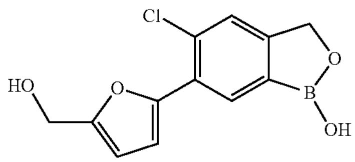 [SMILES: OCc1ccc(-c2cc3c(cc2Cl)COB3O)o1] | 1.13 | 263 | | M1 | |
| 41 | 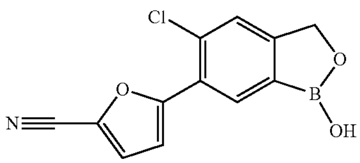 | 1.37 | 258.1 | | M1 | |
| 42 | 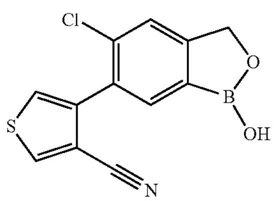 [SMILES: N#Cc1cscc1-c1cc2c(cc1Cl)COB2O] | 1.29 | 274.1 | | M1 | |
| 43 | 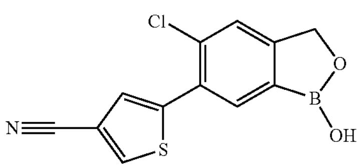 [SMILES: N#Cc1csc(-c2cc3c(cc2Cl)COB3O)c1] | 1.36 | 274.1 | | M1 | |
| 44 | 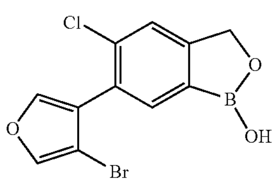 [SMILES: OB1OCc2cc(Cl)c(-c3cocc3Br)cc21] | 1.45 | 311 | | M1 | |
| 45 | 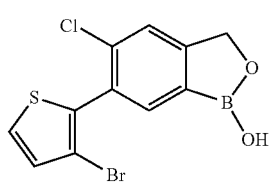 [SMILES: OB1OCc2cc(Cl)c(-c3sccc3Br)cc21] | 1.53 | 327 | | M1 | |

TABLE T1-continued

Characterising data:

| Cmpd No. | Structures | RT (min) | [M − H]⁻ | [M + H]⁺ | Method | MP °C. |
|---|---|---|---|---|---|---|
| 46 | 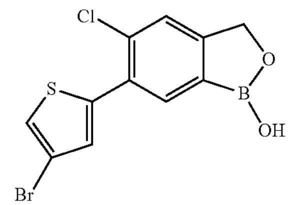 [SMILES: OB1OCc2cc(Cl)c(-c3cc(Br)cs3)cc21] | 1.66 | 326.9 | | M1 | |
| 47 | 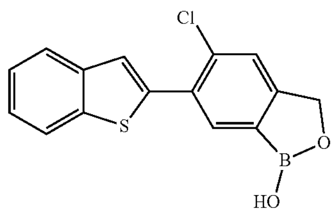 [SMILES: OB1OCc2cc(Cl)c(-c3cc4ccccc4s3)cc21] | 1.72 | 299.1 | | M1 | |
| 48 | 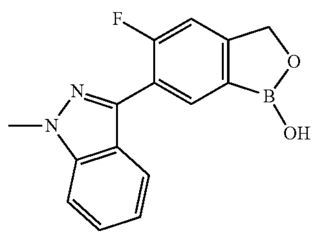 [SMILES: Cn1nc(-c2cc3c(cc2F)COB3O)c2ccccc21] | 1.75 | | 283 | M2 | |
| 49 | 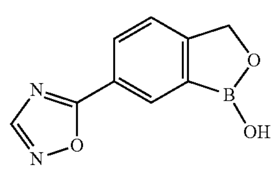 [SMILES: OB1OCc2ccc(-c3ncno3)cc21] | 0.35 | | 203.23 | M3 | 179-180 |
| 50 | 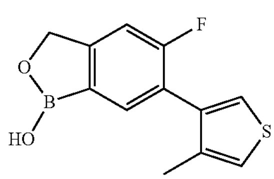 [SMILES: Cc1cscc1-c1cc2c(cc1F)COB2O] | 1.45 | 246.91 | | M4 | — |
| 51 | 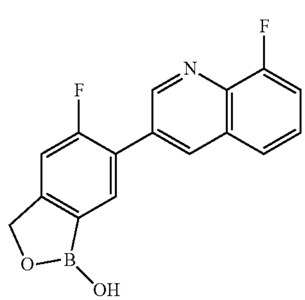 [SMILES: OB1OCc2cc(F)c(-c3cnc4c(F)cccc4c3)cc21] | 1.33 | 295.97 | | M4 | — |
| 52 | 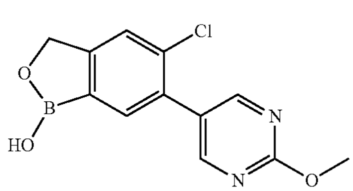 [SMILES: COc1ncc(-c2cc3c(cc2Cl)COB3O)cn1] | 1.16 | 274.98 | | M4 | — |

TABLE T1-continued
Characterising data:
| Cmpd No. | Structures | RT (min) | [M − H]⁻ | [M + H]⁺ | Method | MP ° C. |
|---|---|---|---|---|---|---|
| 53 | 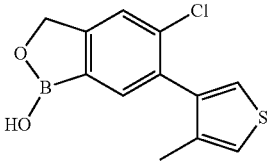 | 1.56 | 262.92 | | M4 | — |
| 54 | 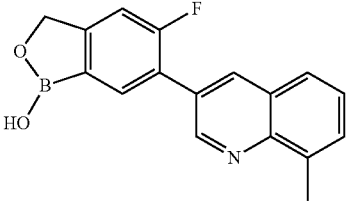 [SMILES: Cc1cccc2cc(-c3cc4c(cc3F)COB4O)cnc12] | 1.42 | 292.01 | | M4 | — |
| 55 | 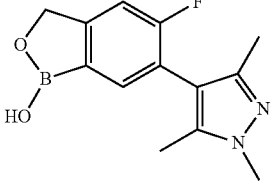 | 1.04 | 259.00 | | M4 | — |
| 56 | 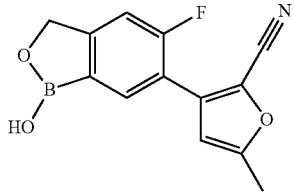 [SMILES: Cc1cc(-c2cc3c(cc2F)COB3O)c(C#N)o1] | 1.37 | 255.95 | | M4 | — |
| 57 | 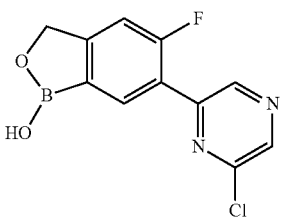 [SMILES: OB1OCc2cc(F)c(-c3cncc(Cl)n3)cc21] | 1.21 | 262.92 | | M4 | — |
| 58 | 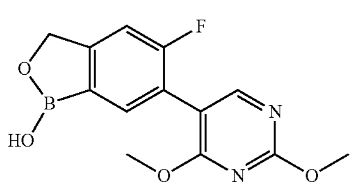 [SMILES: COc1ncc(-c2cc3c(cc2F)COB3O)c(OC)n1] | 1.17 | 289.01 | | M4 | — |
| 59 | 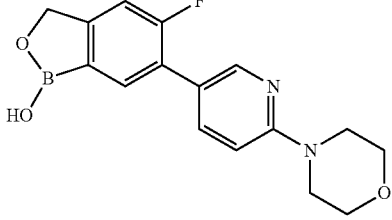 | 0.91 | 312.99 | | M4 | — |

TABLE T1-continued

| Cmpd No. | Structures | RT (min) | [M − H]⁻ | [M + H]⁺ | Method | MP ° C. |
|---|---|---|---|---|---|---|
| 60 | 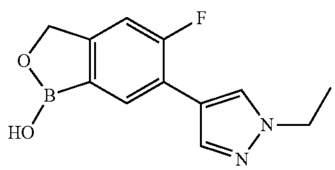 [SMILES: CCn1cc(-c2cc3c(cc2F)COB3O)cn1] | 1.10 | 245.00 | | M4 | — |
| 61 | 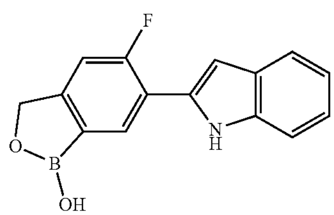 [SMILES: OB1OCc2cc(F)c(-c3cc4ccccc4[nH]3)cc21] | 1.46 | 266.04 | | M4 | — |
| 62 | 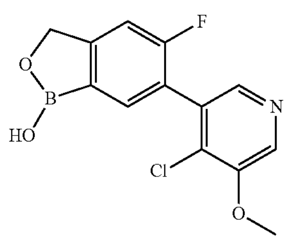 [SMILES: COc1cncc(-c2cc3c(cc2F)COB3O)c1Cl] | 1.38 | 291.99 | | M4 | — |
| 63 | 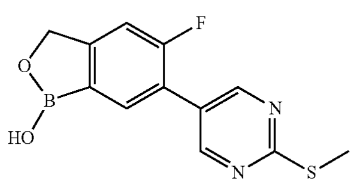 [SMILES: CSc1ncc(-c2cc3c(cc2F)COB3O)cn1] | 1.27 | 274.94 | | M4 | — |
| 64 | 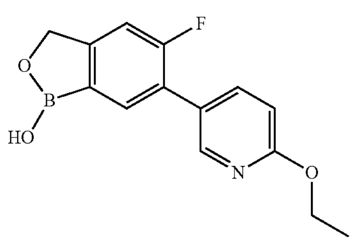 [SMILES: CCOc1ccc(-c2cc3c(cc2F)COB3O)cn1] | 1.41 | 272.01 | | M4 | — |
| 65 | 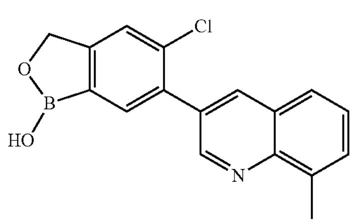 [SMILES: Cc1cccc2cc(-c3cc4c(cc3Cl)COB4O)cnc12] | 1.53 | 307.97 | | M4 | — |
| 66 | 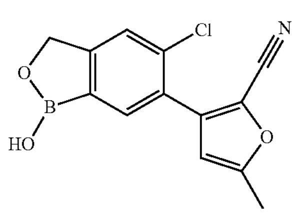 [SMILES: Cc1cc(-c2cc3c(cc2Cl)COB3O)c(C#N)o1] | 1.46 | 271.93 | | M4 | — |

TABLE T1-continued

Characterising data:

| Cmpd No. | Structures | RT (min) | [M − H]⁻ | [M + H]⁺ | Method | MP ° C. |
|---|---|---|---|---|---|---|
| 67 | 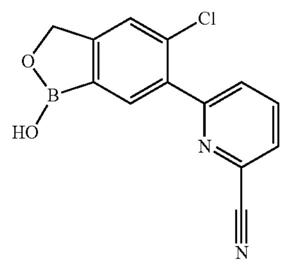 [SMILES: N#Cc1cccc(-c2cc3c(cc2Cl)COB3O)n1] | 1.21 | 268.96 | | M4 | — |
| 68 | 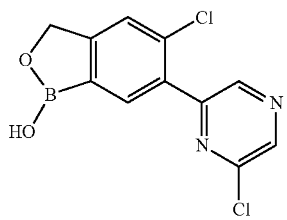 [SMILES: OB1OCc2cc(Cl)c(-c3cncc(Cl)n3)cc21] | 1.29 | 278.89 | | M4 | — |
| 69 | 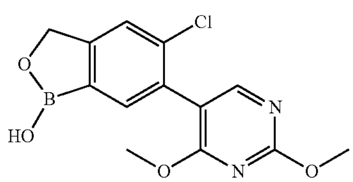 [SMILES: COc1ncc(-c2cc3c(cc2Cl)COB3O)c(OC)n1] | 1.27 | 304.97 | | M4 | — |
| 70 | 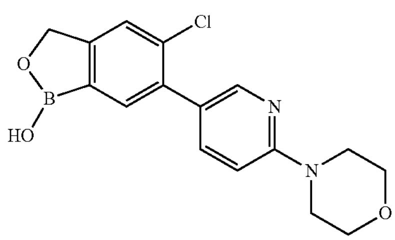 [SMILES: OB1OCc2cc(Cl)c(-c3ccc(N4CCOCC4)nc3)cc21] | 1.00 | 328.95 | | M4 | — |
| 71 | 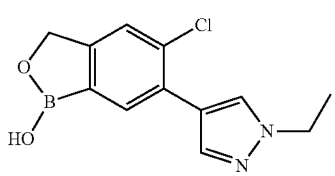 [SMILES: CCn1cc(-c2cc3c(cc2Cl)COB3O)cn1] | 1.19 | 260.99 | | M4 | — |
| 72 | 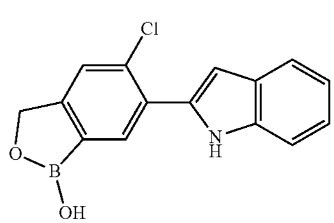 | 1.54 | 281.95 | | M4 | — |
| 73 | 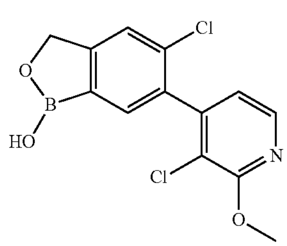 [SMILES: COc1nccc(-c2cc3c(cc2Cl)COB3O)c1Cl] | 1.48 | 307.91 | | M4 | — |

TABLE T1-continued

Characterising data:

| Cmpd No. | Structures | RT (min) | [M − H]⁻ | [M + H]⁺ | Method | MP ° C. |
|---|---|---|---|---|---|---|
| 74 | 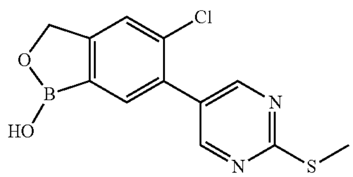 [SMILES: CSc1ncc(-c2cc3c(cc2Cl)COB3O)cn1] | 1.38 | 290.93 | | M4 | — |
| 75 | 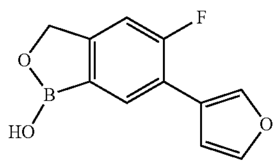 [SMILES: OB1OCc2cc(F)c(-c3ccoc3)cc21] | 1.27 | 216.94 | | M4 | — |
| 76 | 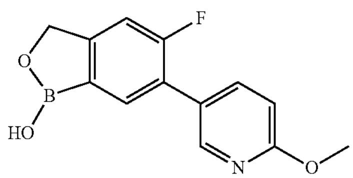 [SMILES: COc1ccc(-c2cc3c(cc2F)COB3O)cn1] | 1.26 | 257.97 | | M4 | — |
| 77 | 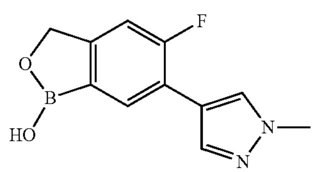 [SMILES: Cn1cc(-c2cc3c(cc2F)COB3O)cn1] | 0.98 | 230.99 | | M4 | — |
| 78 | 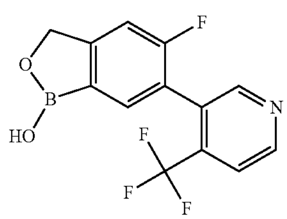 [SMILES: OB1OCc2cc(F)c(-c3cnccc3C(F)(F)F)cc21] | 1.25 | 295.96 | | M4 | — |
| 79 | 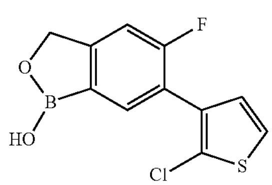 [SMILES: OB1OCc2cc(F)c(-c3ccsc3Cl)cc21] | 1.47 | 266.93 | | M4 | — |
| 80 | 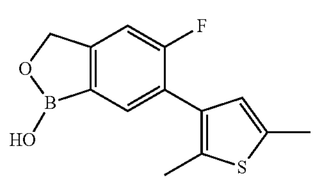 [SMILES: Cc1cc(-c2cc3c(cc2F)COB3O)c(C)s1] | 1.60 | 260.95 | | M4 | — |
| 81 | 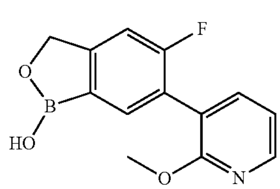 [SMILES: COc1ncccc1-c1cc2c(cc1F)COB2O] | 1.21 | 258.00 | | M4 | — |

TABLE T1-continued

Characterising data:

| Cmpd No. | Structures | RT (min) | [M − H]⁻ | [M + H]⁺ | Method | MP ° C. |
|---|---|---|---|---|---|---|
| 82 | 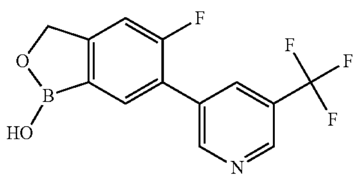 [SMILES: OB1OCc2cc(F)c(-c3cncc(C(F)(F)F)c3)cc21] | 1.38 | 295.98 | | M4 | — |
| 83 | 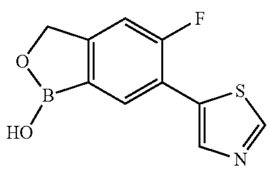 [SMILES: OB1OCc2cc(F)c(-c3cncs3)cc21] | 1.03 | 233.93 | | M4 | — |
| 84 | 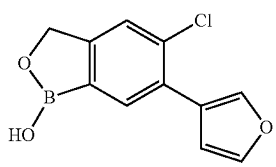 [SMILES: OB1OCc2cc(Cl)c(-c3ccoc3)cc21] | 1.37 | 232.96 | | M4 | — |
| 85 | 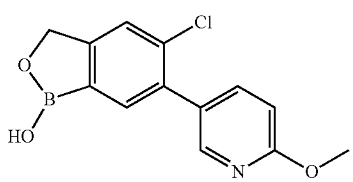 [SMILES: COc1ccc(-c2cc3c(cc2Cl)COB3O)cn1] | 1.37 | 273.93 | | M4 | — |
| 86 | 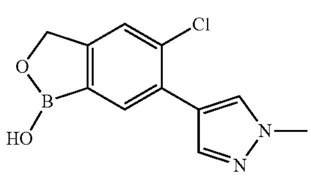 [SMILES: Cn1cc(-c2cc3c(cc2Cl)COB3O)cn1] | 1.07 | 246.96 | | M4 | — |
| 87 | 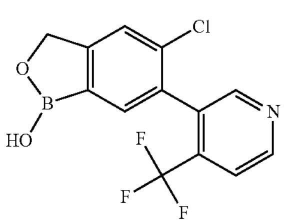 [SMILES: OB1OCc2cc(Cl)c(-c3cnccc3C(F)(F)F)cc21] | 1.34 | 311.90 | | M4 | — |
| 88 | 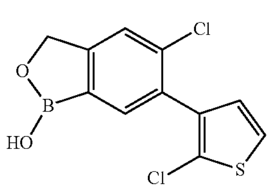 [SMILES: OB1OCc2cc(Cl)c(-c3ccsc3Cl)cc21] | 1.57 | 282.86 | | M4 | — |
| 89 | 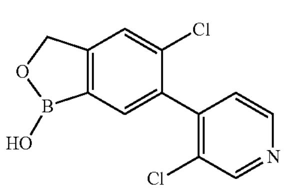 [SMILES: OB1OCc2cc(Cl)c(-c3ccncc3Cl)cc21] | 1.25 | 277.89 | | M4 | — |

TABLE T1-continued

| Cmpd No. | Structures | RT (min) | [M − H]⁻ | [M + H]⁺ | Method | MP ° C. |
|---|---|---|---|---|---|---|
| 90 | (structure: 5-chloro-6-(2,5-dimethylthiophen-3-yl)benzo[c][1,2]oxaborol-1(3H)-ol) | 1.70 | 276.95 | | M4 | — |
| 91 | (structure: 5-chloro-6-(5-(trifluoromethyl)pyridin-3-yl)benzo[c][1,2]oxaborol-1(3H)-ol) | 1.47 | 311.90 | | M4 | — |
| 92 | (structure: 6-(1,2,4-oxadiazol-3-yl)benzo[c][1,2]oxaborol-1(3H)-ol) | | | | | 209-211 |
| 93 | (structure: 7-methoxy-6-(1,3,4-oxadiazol-2-yl)benzo[c][1,2]oxaborol-1(3H)-ol) | | | | | 176-178 |
| 94 | (structure: 5-chloro-6-(1,3,4-oxadiazol-2-yl)benzo[c][1,2]oxaborol-1(3H)-ol) | | | | | 202-204 |
| 95 | (structure: 5-fluoro-6-(1,3,4-oxadiazol-2-yl)benzo[c][1,2]oxaborol-1(3H)-ol) | | | | | 237-239 |
| 96 | (structure: 5-chloro-6-(1,2,4-oxadiazol-3-yl)benzo[c][1,2]oxaborol-1(3H)-ol) | | | | | 180-203 |
| 97 | (structure: 5-fluoro-6-(1,2,4-oxadiazol-3-yl)benzo[c][1,2]oxaborol-1(3H)-ol) | | | | | 226-228 |

Table T1 above shows all the prepared examples with selected melting point and selected NMR data for prepared compounds. $CDCl_3/D_2O$ and DMSO are used as solvents for NMR 400 MHz measurements. No attempt is made to list all characterising data in all cases.

In Table T1 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| m.p. = melting point | b.p. = boiling point. |
|---|---|
| S = singlet | br = broad |
| d = doublet | dd = doublet of doublets |
| t = triplet | q = quartet |
| m = multiplet | ppm = parts per million |

The characteristic values obtained for each compound were the retention time ("$R_t$", recorded in minutes) and the molecular ion as listed in Table 1.
The following LC-MS methods were used to characterize the compounds:
Method: M 1
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY UPLC with the following HPLC gradient conditions
(Solvent A: Water/Methanol 9:1.0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.
Method: M 2
Instrumentation :
Mass Spectrometer :6410 Triple quadrupole Mass Spectrometer from Agilent Technologies
HPLC :Agilent 1200 Series HPLC
Optimized Mass Parameter :
Ionisation method:Electrospray (ESI)
Polarity :positive and Negative Polarity Switch
Scan Type :MS2 Scan
Capillary (kV) :4.00
Fragmentor (V) :100.00
Gas Temperature (° C.) :350
Gas Flow (L/min) :11
Nebulizer Gas (psi) :35
Mass range :110 to 1000 Da
DAD Wavelength range (nm) :190 to 400

Optimized Chromatographic parameter :
Gradient conditions
(Solvent A: Water, 0.1% formic acid and Solvent B: Acetonitrile, 0.1% formic acid)

| Time (minutes) | A (%) | B (%) | Flow rate (ml/min) |
|---|---|---|---|
| 0 | 90 | 10 | 1.8 |
| 2.0 | 0 | 100 | 1.8 |
| 3.0 | 0 | 100 | 1.8 |
| 3.2 | 90 | 10 | 1.8 |
| 4.0 | 90 | 10 | 1.8 |

Type of column: Waters Xterra MS C18; Column length: 30 mm; Internal diameter of column: 4.6 mm; Particle Size: 3.5 µ; Temperature: 30° C.
Method: M 3
Instrumentation
Mass Spectrometer :SQ Detector 2 from Waters; UPLC: Acquity H Class UPLC
Ionisation method :Electrospray (ESI)
Polarity :positive and Negative Polarity Switch
Scan Type :MS1 Scan
Capillary (kV) :3.00, Cone (V): 40, Desolvation Temperature (° C.): 500,
Desolvation Gas Flow (L/Hr): 1000, Cone Gas Flow (L/Hr) :50, Mass range: 0 to 2000, DAD Wavelength range (nm): 200 to 350
Optimized Chromatographic parameter
Gradient conditions :(Solvent A: Water+0.1% formic acid and Solvent B: Acetonitrile)

| Time (minutes) | A (%) | B (%) | Flow rate (ml/min) |
|---|---|---|---|
| 0 | 70 | 30 | 0.5 |
| 0.05 | 70 | 30 | 0.5 |
| 0.8 | 5 | 95 | 0.5 |
| 1.80 | 5 | 95 | 0.5 |
| 2.45 | 70 | 30 | 0.5 |
| 2.50 | 70 | 30 | 0.5 |

Type of column :ACQUITY UPLC BEH C18; Column length: 50 mm, Internal diameter of column: 2.1 mm; Particle Size: 1.7 µ, Temperature :35° C.

BIOLOGICAL EXAMPLES

Fungicidal Action

1 *Phytophthora Infestans*/Tomato/Leaf Disc Preventative (Late Blight)
Tomato leaf disks were placed on water agar in multiwell plates (24-well format) and sprayed with the formulated test compound diluted in water. The leaf disks were inoculated with a spore suspension of the fungus 1 day after application. The inoculated leaf disks were incubated at 16° C. and 75% relative humidity under a light regime of 24 h darkness followed by 12/12 h (light/dark) in a climate cabinet and the activity of a compound was assessed as percent disease control compared to untreated when an appropriate level of disease damage appears in untreated check leaf disks (5-7 days after application). The compounds 11, 13, 15, 16, 17, 27, 29, 30, 39, 42, 56, 93, 94, 95 and 97 (from table T1) at 200 ppm gave at least 80% disease control in this test when compared to untreated control leaf disks under the same conditions, which show extensive disease development.

2 *Plasmopara Viticola*/Grape/Leaf Disc Preventative (Late Blight)

Grape vine leaf disks were placed on water agar in multiwell plates (24-well format) and sprayed with the formulated test compound diluted in water. The leaf disks were inoculated with a spore suspension of the fungus 1 day after application. The inoculated leaf disks were incubated at 19° C. and 80% relative humidity under a light regime of 12/12 h (light/dark) in a climate cabinet and the activity of a compound was assessed as percent disease control compared to untreated when an appropriate level of disease damage appears in untreated check leaf disks (6-8 days after application). The compounds 1, 2, 3, 4, 5, 6, 7, 8, 9, 12, 13, 14, 15, 16, 21, 25, 27, 35, 36, 37, 38, 39, 41, 42, 43, 44, 45, 47, 48, 49, 50, 55, 56, 57, 60, 61, 64, 66, 68, 71, 72, 73, 75, 78, 79, 81, 84, 87, 88, 89 and 91 (from table T1) at 200 ppm gave at least 80% disease control in this test when compared to untreated control leaf disks under the same conditions, which show extensive disease development.

3 *Puccinia Recondita* f. sp. *Tritici*/Wheat/Leaf Disc Preventative (Brown Rust)

Wheat leaf segments cultivated variety (cv) Kanzler were placed on agar in 24-well plates and sprayed with formulated test compound diluted in water. The leaf disks were inoculated with a spore suspension of the fungus 1 day after application. The inoculated leaf segments were incubated at 19° C. and 75% relative humidity under a light regime of 12/12 h (light/dark) in a climate cabinet and the activity of a compound was assessed as percent disease control compared to untreated when an appropriate level of disease damage appears in untreated check leaf segments (7-9 days after application). The compounds 1, 3, 4, 6, 12, 14, 28, 38, 56, 66, 73, 79, 88, 90, 91, 92 and 96 (from table T1) at 200 ppm gave at least 80% disease control in this test when compared to untreated control leaf disks under the same conditions, which show extensive disease development.

4 *Puccinia Recondita* f. sp. *Tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates are stored in darkness at 19° C. and 75% rh. The formulated test compound diluted in water is applied 1 day after inoculation. The leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (6-8 days after application). The compounds 25, 29, 57 and 97 (from table T1) at 200 ppm gave at least 80% disease control in this test when compared to untreated control leaf disks under the same conditions, which show extensive disease development.

5 *Phaeosphaeria Nodorum* (*Septoria Nodorum*)/Wheat/Leaf Disc Preventative (Glume Blotch)

Wheat leaf segments cv Kanzler were placed on agar in a 24-well plate and sprayed with formulated test compound diluted in water. The leaf disks were inoculated with a spore suspension of the fungus 2 days after application. The inoculated test leaf disks were incubated at 20° C. and 75% relative humidity under a light regime of 12/12 h (light/dark) in a climate cabinet and the activity of a compound was assessed as percent disease control compared to untreated when an appropriate level of disease damage appears in untreated check leaf disks (5-7 days after application). The compounds 2, 3, 4, 8, 11, 25, 29, 42, 49, 50, 57, 68, 79, 81, 88, 91, 94 and 97 (from table T1) at 200 ppm gave at least 80% disease control in this test when compared to untreated control leaf disks under the same conditions, which show extensive disease development.

6 *Alternaria Solani*/Tomato/Leaf Disc (Early Blight)

Tomato leaf disks cultivated variety (cv.) Baby were placed on agar in multiwell plates (24-well format) and sprayed with the formulated test compound diluted in water. The leaf disks were inoculated with a spore suspension of the fungus 2 days after application. The inoculated leaf disks were incubated at 23° C./21° C. (day/night) and 80% relative humidity under a light regime of 12/12 h (light/dark) in a climate cabinet and the activity of a compound was assessed as percent disease control compared to untreated when an appropriate level of disease damage appears on untreated check disk leaf disks (5-7 days after application). The compounds 5, 57, 75 and 92 (from table T1) at 200 ppm gave at least 80% disease control in this test when compared to untreated control leaf disks under the same conditions, which show extensive disease development.

7 *Magnaporthe Grisea*(*Pyricularia Oryzae*)/Rice/Leaf Disc Preventative (Rice Blast)

Rice leaf segments cv. Ballila were placed on agar in multiwell plate (24-well format) and sprayed with the formulated test compound diluted in water. The leaf segments were inoculated with a spore suspension of the fungus 2 days after application. The inoculated leaf segments were incubated at 22° C. and 80% rh under a light regime of 24 h darkness followed by 12/12 h (light/dark) in a climate cabinet and the activity of a compound was assessed as percent disease control compared to untreated when an appropriate level of disease damage appears in untreated check leaf segments (5-7 days after application). The compounds 3, 5, 6, 96 and 97 (from table T1) at 200 ppm gave at least 80% disease control in this test when compared to untreated control leaf disks under the same conditions, which show extensive disease development.

8 *Pythium Ultimum*/Liquid Culture (Seedling Damping Off)

Mycelia fragments and oospores of a newly grown liquid culture of the fungus were directly mixed into nutrient broth (potato dextrose broth). After placing a DMSO solution of test compound into a 96-well format microtiter plate, the nutrient broth containing the fungal mycelia/spore mixture was added. The test plates were incubated at 24° C. and the inhibition of growth was determined photometrically 2-3 days after application. The compounds 1, 2, 3, 4, 5, 6, 7, 8, 9, 10, 11, 12, 13, 14, 15, 16, 17, 18, 19, 20, 21, 22, 23, 25, 26, 27, 28, 29, 30, 31, 32, 33, 34, 35, 36, 38, 39, 40, 41, 42, 43, 44, 45, 46, 47, 48, 49, 50, 53, 55, 56, 57, 58, 59, 60, 61, 64, 66, 68, 69, 70, 71, 72, 73, 75, 76, 77, 78, 79, 80, 81, 82, 84, 85, 86, 87, 88, 89, 90, 91, 92, 93, 94, 95, 96 and 97 (from table T1) at 20 ppm gave at least 80% disease control in this test when compared to untreated control leaf disks under the same conditions, which show extensive disease development.

9 *Botryotinia Fuckeliana*(*Botrytis Cinerea*)/Liquid Culture (Gray Mould)

Conidia of the fungus from cryogenic storage were directly mixed into nutrient broth (Vogels broth). After placing a DMSO solution of test compound into a 96-well microtiter plate, the nutrient broth containing the fungal spores was added. The test plates were incubated at 24° C. and the inhibition of growth was determined photometrically 3-4 days after application. The compounds 2, 3, 5, 6, 8, 10, 12, 14, 16, 17, 25, 26, 29, 30, 36, 38, 40, 44, 45, 49, 50, 57, 68, 73, 75, 91, 92, 96 and 97 (from table T1) at 20 ppm gave at least 80% disease control in this test when compared to untreated control leaf disks under the same conditions, which show extensive disease development.

10 *Glomerella Lagenarium(Colletotrichum Ladenarium)*/Liquid Culture (Anthracnose)

Conidia of the fungus from cryogenic storage were directly mixed into nutrient broth (PDB potato dextrose broth). After placing a DMSO solution of test compound into a 96-well microtiter plate, the nutrient broth containing the fungal spores was added. The test plates were incubated at 24° C. and the inhibition of growth was measured photometrically 3-4 days after application. The compounds 2, 3, 4, 5, 6, 8, 10, 14, 15, 16, 17, 18, 21, 22, 23, 25, 26, 27, 28, 29, 30, 31, 34, 35, 36, 37, 38, 39, 40, 41, 42, 43, 44, 45, 46, 49, 50, 53, 60, 72, 73, 75, 79, 80, 81, 82, 84, 88, 89, 90, 91, 92, 93, 94, 95, 96 and 97 (from table T1) at 20 ppm gave at least 80% disease control in this test when compared to untreated control leaf disks under the same conditions, which show extensive disease development.

11 *Mycosphaerella Arachidis(Cercospora Arachidicola)*/Liquid Culture (Early Leaf Spot)

Conidia of the fungus from cryogenic storage were directly mixed into nutrient broth (PDB potato dextrose broth). After placing a DMSO solution of test compound into a 96-well microtiter plate, the nutrient broth containing the fungal spores was added. The test plates were incubated at 24° C. and the inhibition of growth was determined photometrically 4-5 days after application. The compounds 2, 3, 4, 5, 6, 8, 10, 11, 12, 14, 15, 16, 17, 18, 23, 25, 26, 27, 29, 30, 31, 34, 35, 36, 38, 39, 40, 42, 44, 45, 47, 49, 50, 53, 56, 57, 60, 61, 68, 70, 71, 72, 73, 75, 77, 79, 80, 81, 82, 84, 86, 88, 89, 90, 91, 92, 93, 94, 95, 96 and 97 (from table T1) at 20 ppm gave at least 80% disease control in this test when compared to untreated control leaf disks under the same conditions, which show extensive disease development.

12 *Mycosphaerella Graminicola(Septoria Tritici)*/Liquid Culture (Septoria Blotch)

Conidia of the fungus from cryogenic storage were directly mixed into nutrient broth (PDB potato dextrose broth). After placing a DMSO solution of test compound into a 96-well microtiter plate, the nutrient broth containing the fungal spores was added. The test plates were incubated at 24° C. and the inhibition of growth was determined photometrically 4-5 days after application. The compounds 1, 2, 3, 4, 5, 6, 8, 10, 11, 12, 14, 15, 16, 17, 18, 21, 23, 25, 26, 28, 29, 30, 34, 35, 36, 38, 40, 41, 42, 44, 45, 46, 47, 49, 50, 57, 61, 68, 70, 72, 73, 75, 79, 81, 82, 84, 88, 89, 90, 91, 92, 94, 96 and 97 (from table T1) at 20 ppm gave at least 80% disease control in this test when compared to untreated control leaf disks under the same conditions, which show extensive disease development.

13 *Gaeumannomyces Graminis/Liquid Culture* (Take-all of Cereals)

Mycelial fragments of the fungus from cryogenic storage were directly mixed into nutrient broth (PDB potato dextrose broth). After placing a DMSO solution of test compound into a 96-well microtiter plate, the nutrient broth containing the fungal spores is added. The test plates were incubated at 24° C. and the inhibition of growth was determined photometrically 4-5 days after application. The compounds 1, 3, 4, 5, 6, 11, 12, 13, 14, 15, 16, 17, 18, 21, 23, 25, 29, 30, 34, 35, 36, 37, 38, 39, 40, 41, 42, 43, 44, 45, 46, 47, 48, 49, 50, 53, 56, 57, 60, 61, 66, 68, 72, 73, 75, 77, 79, 81, 82, 84, 86, 88, 90, 91, 92, 93, 94, 95, 96 and 97 (from table T1) at 20 ppm gave at least 80% disease control in this test when compared to untreated control leaf disks under the same conditions, which show extensive disease development.

14 *Monographella Nivalis(Microdochium Nivale)*/Liquid Culture (Foot Rot Cereals)

Conidia of the fungus from cryogenic storage were directly mixed into nutrient broth (PDB potato dextrose broth). After placing a DMSO solution of test compound into a 96-well microtiter plate, the nutrient broth containing the fungal spores was added. The test plates were incubated at 24° C. and the inhibition of growth was determined photometrically 4-5 days after application. The compounds 1, 2, 3, 4, 5, 6, 11, 12, 13, 14, 15, 16, 17, 18, 20, 21, 22, 23, 24, 25, 26, 27, 29, 30, 31, 32, 34, 35, 36, 37, 38, 39, 40, 41, 42, 43, 44, 45, 46, 47, 48, 49, 50, 53, 56, 57, 58, 60, 61, 64, 68, 70, 71, 72, 73, 75, 76, 79, 80, 81, 82, 84, 85, 86, 87, 88, 89, 90, 91, 92, 96 and 97 (from table T1) at 20 ppm gave at least 80% disease control in this test when compared to untreated control leaf disks under the same conditions, which show extensive disease development.

15 *Fusarium Culmorum*/Liquid Culture (Head Blight)

Conidia of the fungus from cryogenic storage were directly mixed into nutrient broth (PDB potato dextrose broth). After placing a (DMSO) solution of the test compounds into a microtiter plate (96-well format), the nutrient broth containing the fungal spores was added. The test plates were incubated at 24° C. and the inhibition of growth was determined photometrically 3-4 days after application. The compounds 1, 2, 3, 4, 5, 6, 8, 10, 11, 12, 14, 15, 16, 17, 18, 20, 25, 26, 29, 34, 35, 36, 38, 39, 40, 42, 44, 45, 49, 50, 57, 72, 73, 75, 84, 88, 91, 92, 96 and 97 (from table T1) at 20 ppm gave at least 80% disease control in this test when compared to untreated control leaf disks under the same conditions, which show extensive disease development.

16 *Thanatephorus Cucumeris(Rhizoctonia Solani)*/Liquid Culture (Foot Rot, Damping-Off)

Mycelia fragments of a newly grown liquid culture of the fungus were directly mixed into nutrient broth (PDB potato dextrose broth). After placing a DMSO solution of the test compounds into a 96-well microtiter plate at an application rate of 200 ppm, the nutrient broth containing the fungal material was added. The test plates were incubated at 24° C. and the inhibition of growth was determined photometrically 3-4 days after application. The compounds 2, 3, 5, 6, 12, 14, 15, 25, 29, 35, 36, 38, 39, 44, 45, 49, 50, 56, 72, 73, 75, 79, 84, 88, 90, 91, 92, 96 and 97 (from table T1) at 20 ppm gave at least 80% disease control in this test when compared to untreated control leaf disks under the same conditions, which show extensive disease development.

17 *Sclerotinia Sclerotiorum*/Liquid Culture (Cottony Rot)

Mycelia fragments of a newly grown liquid culture of the fungus were directly mixed into nutrient broth (PDB potato dextrose broth). After placing a (DMSO) solution of the test compounds into a microtiter plate (96-well format) the nutrient broth containing the fungal material was added. The test plates were incubated at 24° C. and the inhibition of growth was determined visually 3-4 days after application. The compounds 2, 3, 5, 6, 8, 10, 11, 12, 14, 15, 16, 17, 18, 21, 25, 26, 29, 30, 36, 38, 40, 42, 44, 45, 49, 50, 57, 61, 68, 73, 75, 79, 81, 82, 84, 88, 91, 92, 94, 95, 96 and 97 (from table T1) at 20 ppm give at least 80% disease control in this test when compared to untreated control leaf disks under the same conditions, which show extensive disease development.

The invention claimed is:

1. A compound of formula (I)

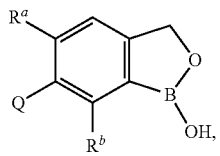

wherein
- $R^a$ and $R^b$ is H, fluorine, chlorine, bromine, cyano, nitro, $C_1$-$C_4$alkyl which can be substituted by one to five $R^5$, $C_1$-$C_4$alkoxy which can be substituted by one to five $R^5$, $C_1$-$C_4$haloalkyl which can be substituted by one to five $R^{5a}$;
- Q is a five- to ten-membered monocyclic or bicyclic ring system linked directly via a carbon atom to the rest of the molecule, said ring system is aromatic and contains 1 to 4 ring members selected from the group consisting of nitrogen, oxygen, —C(O)— and —S(O)$_m$—, it not being possible for each ring system to contain more than 2 oxygen atoms and more than 2 sulfur atoms, said five- to ten-membered ring system which can be substituted by one to five $R^5$;
- $R^5$ is independently selected from halogen, —OH, —CN, —NO$_2$, —NR$^6$R$^7$, $C_{1-4}$alkyl, $C_{1-4}$haloalkyl, $C_{1-4}$alkoxy, $C_{1-4}$haloalkoxy, $C_{3-6}$cycloalkyl, $C_2$-$C_6$alkenyl, $C_{2-6}$alkynyl, $C_{1-4}$alkylthio, $C_{1-4}$haloalkylthio, —C(O)H, —C(O)(C$_{1-4}$alkoxy), —C(O)(C$_{1-4}$alkyl), —C(O)—NH—(C$_{1-4}$alkyl), —C(O)—N(C$_{1-4}$alkyl)$_2$, $C_{1-4}$alkoxy-$C_1$-$C_4$alkyl, hydroxyimino, $C_1$-$C_4$alkoximino, $C_1$-$C_4$alkoximino $C_1$-$C_4$alkyl, $C_1$-$C_4$alkylendioxyl, —OC(O)NH(C$_{1-4}$alkyl), —OC(O)N(C$_{1-4}$alkyl), —OC(O)N(C$_{1-4}$alkyl)(C$_{1-4}$alkyl)(C$_{1-4}$alkyl),—NHC(O)(C$_{1-4}$alkyl), —NHC(O)(C$_{1-4}$alkoxy), —N(C$_{1-4}$alkyl)C(O)(C$_{1-4}$alkoxy), —N(C$_{1-4}$alkyl) C(O)(C$_{1-4}$alkoxy), —OC(O)(C$_{1-4}$alkyl), —C(=N—O—(C$_{1-4}$alkyl)—H, —C(=N—O—(C$_{1-4}$alkyl)-C$_1$-C$_4$alkyl;
- or $R^5$ is independently selected from a -X-(6 to 10 membered-aryl) group which can be substituted by one to five substituents selected halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;
- or $R^5$ is independently selected from a -X-linked-5- or 6-membered heteroaryl group which comprises one or two or three heteroatoms selected from or two N, O and S which can be substituted by one to five substituents selected from halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;
- or $R^5$ is independently selected from a -X-linked-5- or 6-membered heterocycloalkyl group which comprises one or two or three heteroatoms selected from or two N, 0 and S which can be substituted by one to five substituents selected from halogen, $C_1$-$C_4$alkyl, $C_1$-$C_4$haloalkyl, $C_1$-$C_4$alkoxy, —CN, —NO$_2$, —NR$^6$R$^7$, $C_3$-$C_6$cycloalkyl;
- $R^{5a}$ is independently selected from $C_1$-$C_4$alkyl, $C_1$-$C_4$haloalkyl, $C_1$-$C_4$alkoxy, $C_1$-$C_4$haloalkoxy, —OH, —CN, —NO$_2$;
- $R^6$ and $R^7$ are independently H, —C$_{1-4}$alkyl —C$_{2-4}$alkenyl, —C$_{2-4}$alkynyl or combine with the interjacent nitrogen to form a five- or six-membered heterocyclic ring which may comprise additionally to the interjacent nitrogen atom one or two heteroatoms selected from N, O or S atoms, it not being possible for each ring system to contain more than 2 oxygen atoms and more than 2 sulfur atoms, and this five- or six-membered heterocyclic ring is unsubstituted or this five- or six-membered heterocyclic ring which can be substituted by one to five $R^5$;
- X is a direct bond or a bridge selected from —O—, —S(O)$_m$— or —NH—;
- m is 0, 1 or 2;

or an agrochemically acceptable salt or N-oxide thereof.

2. The compound of formula claim 1, wherein $R^a$ and $R^b$ independently are H, fluorine, chlorine, bromine, cyano, nitro, $C_1$-$C_4$alkyl, $C_1$-$C_4$alkoxy, $C_1$-$C_4$haloalkyl.

3. The compound of claim, wherein $R^5$ independently selected from the group consisting of chlorine, cyano, hydroxyl, $C_1$-$C_4$alkyl, $C_1$-$C_4$alkylthio, —C(O)H, —C(O)(C$_{1-4}$alkyl), hydroxyimino, $C_1$-$C_4$alkoximino $C_1$-$C_4$alkoximino $C_1$-$C_4$alkyl, N-morpholine.

4. The compound of claim 1, wherein Q is selected from the group consisting of J-1 to J-59 (and #— represents the point of attachment of the heterocycle Q to the benzoxoborol moiety):

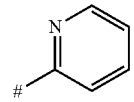
J-1

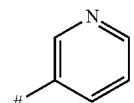
J-2

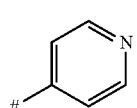
J-3

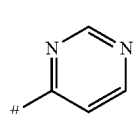
J-4

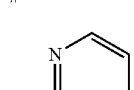
J-5

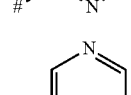
J-6

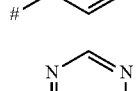
J-7

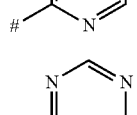
J-8

-continued
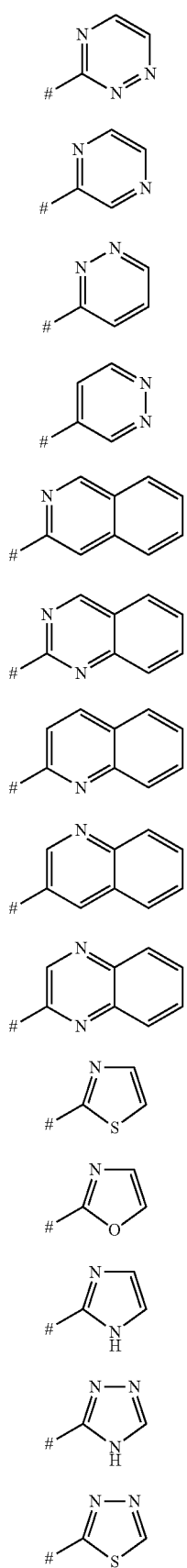
J-9
J-10
J-11
J-12
J-13
J-14
J-15
J-16
J-17
J-18
J-19
J-20
J-21
J-22
-continued
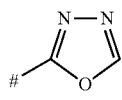 J-23
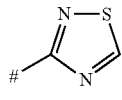 J-24
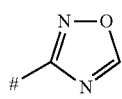 J-25
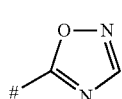 J-26
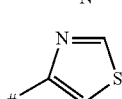 J-27
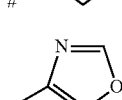 J-28
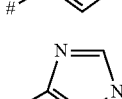 J-29
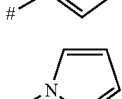 J-30
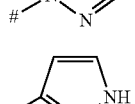 J-31
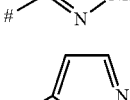 J-32
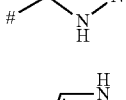 J-33
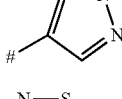 J-34
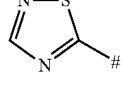 J-35
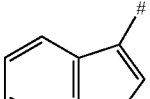 J-36
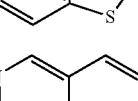 J-37
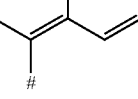
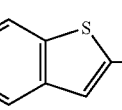

J-38 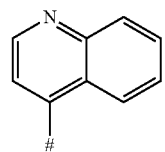

J-39 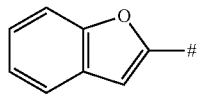

J-40 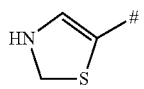

J-41 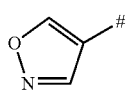

J-42 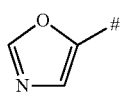

J-43 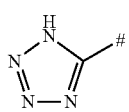

J-44 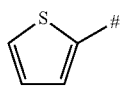

J-45 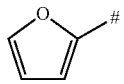

J-46 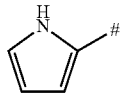

J-47 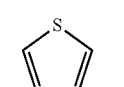

J-48 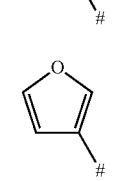

J-49 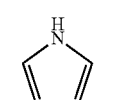

J-50 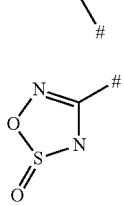

J-51 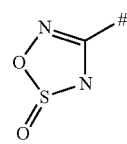

J-52 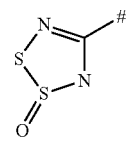

J-53 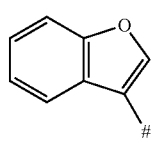

J-54 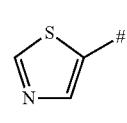

J-55 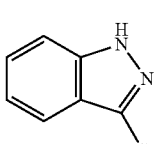

J-56 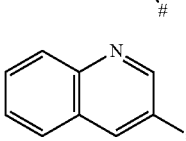

J-57 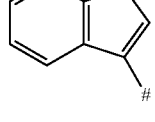

J-58 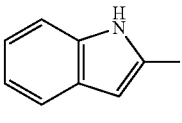

J-59 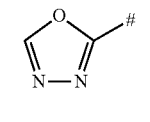

wherein each group J-1 to J-59 which can be substituted by one to five $R^5$.

5. The compound of claim 4, wherein Q is selected from the group consisting of Q is selected from the group consisting of J-1, J-2, J-3, J-10, J-18,19, J-23, J-25, J-26, J-27, J-32, J-33, J-37, J-39, J-41, J-42, J-43, J-44, J-45, J-46, J-47, J-48, J-53, J-54, J-55, J-56, J-57, J-58, and J-59.

6. A method of controlling or preventing infestation of useful plants by phytopathogenic microorganisms, wherein the compound of formula (I) as defined in claim 1 or a composition comprising the compound of formula (I) as defined in claim 1 as active ingredient, is applied to the plants, to parts thereof or the locus thereof.

7. A composition for controlling and protecting against phytopathogenic microorganisms, comprising the compound of formula (I) as defined in claim 1 and at least one auxiliary.

8. The method of claim 6, wherein controlling further includes controlling phytopathogenic diseases on useful plants or plant propagation material thereof.

9. The composition of claim 7, further comprising at least one additional active ingredient.

* * * * *